(12) United States Patent
Kido et al.

(10) Patent No.: US 6,388,122 B1
(45) Date of Patent: May 14, 2002

(54) TRYPTASE INHIBITOR AND NOVEL GUANIDINO DERIVATIVES

(75) Inventors: Hiroshi Kido, Tokushima; Hisao Nakai, Mishima-gun, both of (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/155,868

(22) PCT Filed: Apr. 9, 1997

(86) PCT No.: PCT/JP97/01215

§ 371 Date: Oct. 7, 1998

§ 102(e) Date: Oct. 7, 1998

(87) PCT Pub. No.: WO97/37969

PCT Pub. Date: Oct. 16, 1997

(30) Foreign Application Priority Data

Apr. 10, 1996 (JP) .............................................. 8-113159

(51) Int. Cl.[7] ...................... C07C 229/38; C07C 229/52

(52) U.S. Cl. .............................. 560/34; 560/12; 560/16; 560/35; 560/39; 560/42; 560/43; 560/55; 514/255.01; 514/330; 514/423; 514/533; 514/534; 514/535; 514/634; 514/646; 544/391; 546/226; 548/540

(58) Field of Search .............................. 560/12, 34, 16, 560/35, 39, 42, 43, 55; 546/226; 548/540; 514/255.01, 330, 423, 533, 534, 535, 634, 646; 544/391; 564/248

(56) References Cited

U.S. PATENT DOCUMENTS

| | | |
|---|---|---|
| 3,652,650 A | 3/1972 | Fujii et al. |
| 3,652,651 A | 3/1972 | Fujii et al. |
| 3,751,447 A | 8/1973 | Fujii et al. |
| 3,751,477 A * | 8/1973 | Fujii et al. .................. 260/473 |
| 3,824,267 A | 7/1974 | Ito et al. |
| 4,021,472 A | 5/1977 | Fujii et al. |
| 4,224,342 A | 9/1980 | Fujii et al. |
| 4,283,418 A | 8/1981 | Fujii et al. |
| 4,310,533 A | 1/1982 | Uegai et al. |
| 4,490,388 A | 12/1984 | Fujii et al. |
| 4,514,416 A | 4/1985 | Fujii et al. |
| 4,746,737 A | 5/1988 | Fujii et al. |
| 4,801,603 A | 1/1989 | Souda et al. |
| 4,845,242 A | 7/1989 | Powers et al. |
| 5,432,178 A * | 7/1995 | Nakai et al. ................. 514/255 |

FOREIGN PATENT DOCUMENTS

| | | |
|---|---|---|
| EP | A222608 | 5/1987 |
| EP | 0287036 | 10/1988 |
| EP | 0350840 | 1/1990 |

(List continued on next page.)

OTHER PUBLICATIONS

Database CAPLUS on STN, Acc. No. 1979:575040, Fujii et al., 'P–guanidinobenzoate esters.' JP 54070240 (abstract), 1979.*

Database CAPLUS on STN, Acc. No. 1994:595917, Inada et al., 'Aprotinin or other protease inhibitors for treatment of mite–induced allergy.' JP 06192085 (abstract), 1994.*

"Tryptase in Rat Mast Cells: Properties and Inhibition by Various Inhibitors in Comparison with Chymase"; Mutumi Muramatu et al; Biol. Chem. Hoppe–Seyler, vol. 369, pp. 617–625, Jul. 1988.

Search Report dated Oct. 11, 2000.

Chem. Pharm. Bull., 32, 4466–4477 (1984).

*Primary Examiner*—Johann Richter
*Assistant Examiner*—Brian J. Davis
(74) *Attorney, Agent, or Firm*—Stevens, Davis, Miller & Mosher, L.L.P.

(57) ABSTRACT

A tryptase inhibitor comprising as an active ingredient at least one member selected from among guanidinoaliphatic acid derivatives of the formula (I), guanidinobenzoic acid derivatives of the formula (II), guanidinophenol derivatives of the formula (III), amidinophenol derivatives of the formula (IV), and novel guanidinophenol derivatives of the formula (V) (in the formulae, Gu is guanidino).

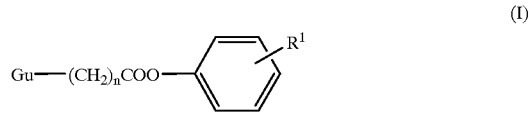

(I)

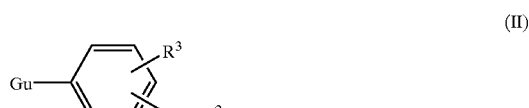

(II)

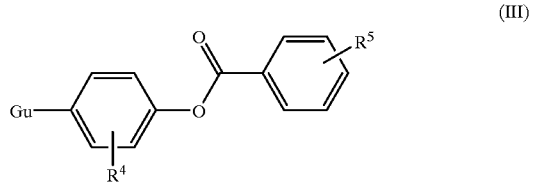

(III)

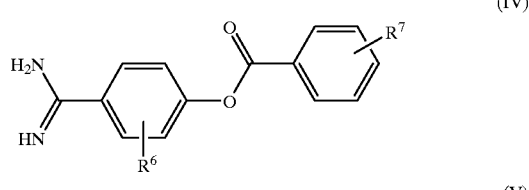

(IV)

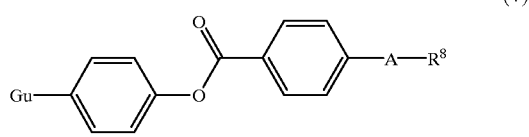

(V)

16 Claims, No Drawings

FOREIGN PATENT DOCUMENTS

| | | |
|---|---|---|
| EP | A588655 | 3/1994 |
| EP | A656349 | 6/1995 |
| EP | A703216 | 3/1996 |
| GB | A2083818 | 3/1982 |
| JP | 4533175 | 1/1970 |
| JP | 4911842 | 1/1974 |
| JP | 50004038 | 1/1975 |
| JP | 5069035 | 6/1975 |
| JP | 5116631 | 2/1976 |
| JP | 5175042 | 6/1976 |
| JP | 5315412 | 2/1978 |
| JP | 53147044 | 12/1978 |
| JP | 5476532 | 6/1979 |
| JP | 55100356 | 7/1980 |
| JP | 56110664 | 9/1981 |
| JP | 61286361 | 12/1986 |
| JP | 61286362 | 12/1986 |
| JP | 1272523 | 10/1989 |
| JP | 5286922 | 11/1993 |
| JP | 6192085 | 7/1994 |
| JP | 8113159 | 4/1996 |
| JP | 8333249 | 12/1996 |
| WO | 9420527 | 9/1994 |

* cited by examiner

TRYPTASE INHIBITOR AND NOVEL GUANIDINO DERIVATIVES

TECHNICAL FIELD

The present invention relates to a tryptase inhibitor comprising, as an active ingredient, one or more kinds of substances selected from guanidinoaliphatic acid derivatives, guanidinobenzoic acid derivatives, guanidinophenol derivatives, amidinophenol derivatives, and nontoxic salts, acid addition salts or hydrates thereof, and to novel guanidinophenol derivatives and nontoxic salt, acid addition salt or hydrate thereof. More specifically, the present invention relates to a tryptase inhibitor comprising, as an active ingredient, one or more kinds of substances selected from guanidinoaliphatic acid derivatives, guanidinobenzoic acid derivatives, guanidinophenol derivatives and amidinophenol derivatives represented by the formulae (I) to (IV)

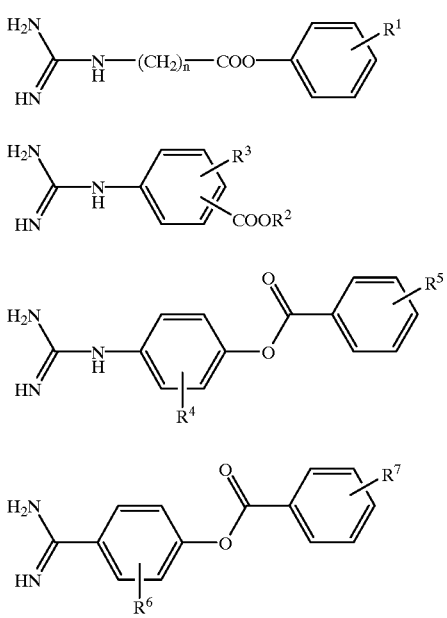

(in the formulae, all the symbols represent the same meanings as hereafter defined), or nontoxic salts, acid addition salts or hydrates thereof, and to pharmaceuticals comprising, as an active ingredient, novel guanidinophenol derivatives represented by the formula (V)

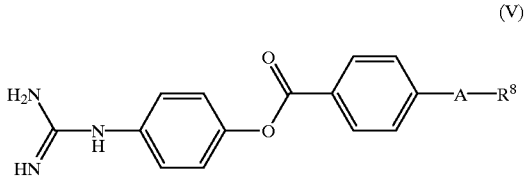

(in the formulae, all the symbols represent the same meanings as hereafter defined), or nontoxic salts, acid addition salts or hydrates thereof.

BACKGROUND ART

Tryptase is an intracellular trypsin-type protease that was isolated and purified from the human lung by Smith, et al. in 1984 (see T. J. Smith, M. W. Houglandi D. A. Johnson, J. Biol. Chem., 25, 11046 (1984)).

Tryptase is thought to belong to the trypsin-type protease since (1) tryptase cleaves the C-terminal of basic amino acids (especially arginine) as well as trypsin, (2) it decomposes common trypsin artificial substrates, and (3) its protease activity is inhibited by the trypsin inhibitors.

Tryptase is, however, categorized into a family having different properties from trypsin on the basis that (1) tryptase cannot decompose Arg-MCA (arginine-methylcoumarinamide) and Arg-bNA (arginine-β-naphthylamide) which are artificial substrates highly decomposed by trypsin, (2) it highly decomposes Boc-Ile-Gly-Arg-MCA(t-butoxycarbonyl-isoleucine-glycine-arginine-methylcoumarinamide) which is an artificial substrate of blood coagulation factor Xa that is hard to be decomposed by trypsin, and (3) it limitedly decomposes prothrombin to produce thrombin while trypsin nonlimitedly decomposes most prothrombin. Additionally, tryptase is completely different from the other protease (e.g., plasmin, thrombin, kallikrein, elastase. etc.) in the structure, localizing cells, physiological functions and so on.

Tryptase is known as it exists in the following cells, and however, the structure thereof varies depending upon the localizing cell.

(1) Tryptase in Mast Cell (Tryptase M)

Tryptase M localizes in the soluble state in the typical (connective tissue) mast cell, atypical (membrane) mast cell and the histamine granules of basocytes. Human tryptase M was isolated and purified by Schwartz, et al. (see L. B. Schwartz, R. A. Lewis, K. F. Ansten, J. Biol. Chem., 25, 11939 (1981)). This enzyme is a heterotetramer having a molecular weight of 144,000 composed of two molecules of subunit having a molecular weight of 37,000 and two having that of 35,000.

(2) Tryptase in $T_4$ Lymphocyte (Tryptases $TL_1$, $TL_2$ and $TL_3$)

Tryptases $TL_1$, TL2 and $TL_3$ were isolated and purified from the bulk-cultured cells of the Molt 4 clone 8 strain, which is one of the $T_4$ lymphocytes, by Kido, Katunuma, et al. (see H. Kido, A. Fukutomi, N. Katunuma, J. Biol. Chem., 2, 21979 (1991)). Tryptases $TL_1$ and $TL_2$ were purified from the cell membrane, and Tryptase $TL_3$ was purified from the Golgi body.

(3) Tryptase in Clara Cells (Tryptase Clara)

Tryptase Clara was isolated and purified from the bronchial membrane secretory cell (Clara cell) by Kido, Katsunuma, et al. (see H. Kido, Y. Yokogoshi, K. Sakai, M. Tashiro, Y. Kishino, A. Fukutomi, N. Katunuma, J. Biol. Chem., 267, 13573 (1992)). The molecular weight of this enzyme is 30,000 by means of SDS-PAGE (SDS-polyacrylamide gel electrophoresis) in the presence of a reducing agent, or 180,000 by gel filtration.

The physiological functions of the above-mentioned tryptase have been reported as follows:

(1) decomposition of fibrinogen (see J. Immunol., 135, 2762 (1985)), (2) decomposition of polymer kininogen and fibrin (see J. Immunol., 135, 2762 (1985)), (3) activation of single-stranded urokinase type plasminogen activator (see J. Biol. Chem., 269, 9416 (1994)), (4) formation of complement C3a from C3 (see J. Immunol., 130, 1891 (1983)), (5) decomposition of VIP (vaso active intestinal peptide) and CGRP (calcitonin gene-related peptide) (see Allergy, 27, 90 (1990), J. Pharmacol. Exp. Ther., 244, 133 (1988), and J. Pharmac. and Exp. Ther., 248, 947 (1989)), (6) release of IL-8 from the bronchial epithelial cell and stimulation to express ICAM-1 (see J. Immunol., 15, 275 (1996)), (7) decomposition of fibronectin (see J. Cell. Biochem., 50, 337 (1992)).

(8) stimulation to proliferate fibroblast (see J. Crin. Invest., 88, 493 (1991)), (9) decomposition of collagen IV,

(10) activation of promatrix metalloprotease 3 (proMMP-3) (J. Crin. Invest., 84, 1657 (1989)),

(11) activation of stromelysin, and

(12) decomposition of 72 kD gelatomase.

Studies on the relation of tryptase to condition of disorder have been reported as follows.

(1) Tryptase at high level exists in the washing water of the bronchus of asthma patients.

(2) The tryptase released from the mast cell in the site of pulmonary fibrosis induces inflammation reaction mediated by various mediators.

(3) The tryptase released from the mast cell in the site of chronic rheumatism enhances collagenase activity.

(4) The tryptase in the process of infection of Sendai virus elevates the ability of membrane fusion and infection of the virus.

Tryptase inhibitors are thought to be useful for prevention and/or treatment of various diseases caused by tryptase. In consideration of the relation between the physiological function of tryptase and condition of disorder, the diseases are exemplified by asthma, pulmonary fibrosis, interstitial pneumonitis, nephritis, hepatic fibrosis, hepatitis, cirrhosis, scleroderma, psoriasis, atopic dermatitis, chronic rheumatism, influenza, Crohn's disease, inflammatory intestinal diseases, ulcerative colitis, nasal allergy, atherosclerosis, etc.

Recently, some studies on the tryptase inhibitors of non-peptide compounds having an amidino or guanidino group have been reported (see J. Stuerzebecher, et. al., Biol. Chem. Hoppe-Seyler, 37, 1025 (1992), G. H. Caughey, et. al., J. Pharmacol. Exp. Ther. 2, 676 (1993), C. H. Kam, et al., Arch. Biochem. Biophys., 316, 808 (1995), U.S. Pat. No. 4,845,242, U.S. Pat. No. 5,089,634, U.S. Pat. No. 5,324,648, and PCT Publication No. 9,427,958).

Disclosure of the Invention

In order to find tryptase inhibitors from the points of view above, the present inventors intensively studied to find that guanidinoaliphatic acid derivatives represented by the formula (I), guanidinobenzoic acid derivatives represented by the formula (II), guanidinophenol derivatives represented by the formula (III) and amidinophenol derivatives represented by the formula (IV) have potent tryptase inhibitory activity. Thus, the present invention is completed.

Further, it was found that novel guanidinophenol derivatives represented by the formula (V) have potent tryptase inhibitory activity.

Moreover, it was found that the novel guanidinophenol derivatives represented by the formula (V) have potent antagonistic inhibitory activity on a variety of proteinases (e.g., trypsin, plasmin, thrombin and kallikrein), phospholipase $A_2$ ($PLA_2$) and/or leukotriene $B_4$ ($LTB_4$).

That is, the present invention relates to (1) a tryptase inhibitor comprising, as an active ingredient, guanidinoaliphatic acid derivatives represented by the formula (I)

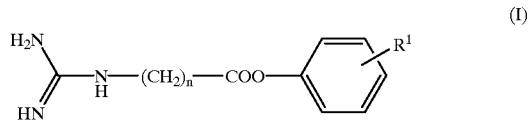

(in the formula, $R^1$ represents a hydrogen atom, a halogen atom, a nitro group, an alkyl group, an alkoxyl group, a carboxyl group or an alkoxycarbonyl group, and n represents an integer of 3 to 6), or nontoxic salts, acid addition salts or hydrates thereof;

(2) a tryptase inhibitor comprising, as an active ingredient, guanidinobenzoic acid derivatives represented by the formula (II)

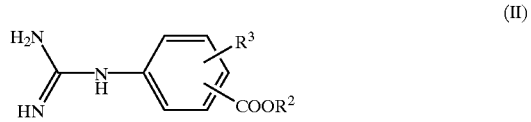

(in the formula, $R^2$ represents a phenyl group, a naphthyl group, a substituted phenyl group or a substituted naphthyl group, and $R^3$ represents one of various substituting groups), or nontoxic salts, acid addition salts or hydrates thereof;

(3) a tryptase inhibitor comprising, as an active ingredient, guanidinophenol derivatives represented by the formula (III)

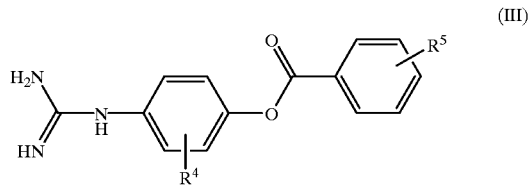

(in the formula, $R^4$ and $R^5$ represent various substituting groups), or nontoxic salts, acid addition salts or hydrates thereof;

(4) a tryptase inhibitor comprising, as an active ingredient, amidinophenol derivatives represented by the formula (IV)

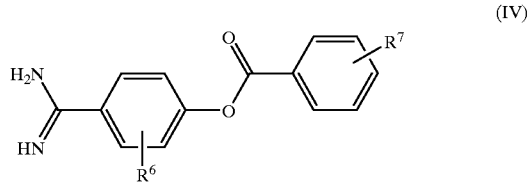

(in the formula, R6 and $R^7$ represent various substituting groups), or nontoxic salts, acid addition salts or hydrates thereof;

(5) guanidinophenol derivatives represented by the formula (V)

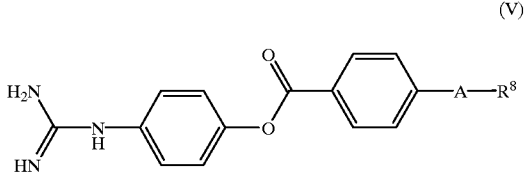

[in the formula, A represents a group of the following formula:

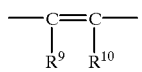

(in the group, $R^9$ and $R^{10}$ each represents independently a hydrogen atom or a $C_{1-4}$ alkyl group),
$R^8$ represents a group selected from the following formulae:

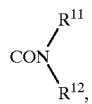

(i)

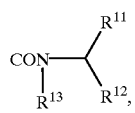

(ii)

or

(iii)

(in the groups, $R^{11}$, $R^{12}$ and $R^{13}$ each represents independently
(1) a hydrogen atom,
(2) a phenyl group,
(3) a $C_{1-4}$ alkyl group substituted by a phenyl group,
(4) a $C_{1-10}$ alkyl group,
(5) a $C_{1-10}$ alkoxyl group,
(6) a $C_{2-10}$ alkenyl group having 1 to 3 double bonds,
(7) a $C_{2-10}$ alkynyl group having 1 to 2 triple bonds,
(8) a group of formula: $R^{15}$—$COXR^{16}$
(in the group, $R^{15}$ represents a single bond or a $C_{1-8}$ alkylene group, X represents an oxygen atom or an NH-group, and
$R^{16}$ represents a hydrogen atom, a $C_{1-4}$ alkyl group, a phenyl group or a $C_{1-4}$ alkyl group substituted by a pheny group), or
(9) a $C_{3-7}$ cycloalkyl group;

represents a 4–7 membered monocyclic heteroring containing 1 to 2 nitrogen atoms,
$R^{14}$ represents a hydrogen atom, a $C_{1-4}$ alkyl group substituted by a phenyl group or a group of formula: $COOR^{17}$ (in the group, $R^{17}$ represents a hydrogen atom, a $C_{1-4}$ alkyl group or a $C_{1-4}$ alkyl group substituted by a phenyl group);
provided that $R^{11}$, $R^{12}$ and $R^{13}$ do not represent simultaneously hydrogen atoms, and when at least one group among $R^{11}$, $R^{12}$ and
$R^{13}$ represents a group having a t-butoxycarbonyl group, the other groups do not represent groups having a carboxyl group.] or nontoxic salts, acid addition salts or hydrates thereof;
(6) methods of preparing the guanidinophenol derivatives represented by the formula (V), and nontoxic salts, acid addition salts or hydrates thereof;
(7) pharmaceuticals comprising, as an active ingredient, the guanidinophenol derivatives represented by the formula (V), or nontoxic salts, acid addition salts or hydrates thereof;
(8) agents for prevention and/or treatment of asthma, pulmonary fibrosis, hepatitis, interstitial pneumonitis, nephritis, hepatic fibrosis, hepatitis, cirrhosis, scleroderma, psoriasis, atopicdermatitis, chronicrheumatism, influenza, Crohn's disease, inflammatory intestinal diseases, ulcerative colitis, nasal allergy, atherosclerosis which comprise, as an active ingredient, the guanidinoaliphatic acid derivatives represented by the formula (I), the guanidinobenzoic acid derivatives represented by the formula (II), the guanidinophenol derivatives represented by the formula (III), the amidinophenol derivatives represented by the formula (IV), or nontoxic salts, acid addition salts or hydrates thereof; and
(9) agents for prevention and/or treatment of chronic rheumatism, inflammatory intestinal diseases, psoriasis, stomach diseases induced by non-steroidal antiinflammatory drugs, adult respiratory distress syndrome, myocardial infarction, allergic rhinitis, hemodialysis-inducing neutropenia, late asthma, various inflammatory diseases, allergic diseases, disseminated intravascular coagulation, pancreatitis, severe stages thereof and multiple organ failure which comprise, as an active ingredient, the guanidinophenol derivatives represented by the formula (V), or nontoxic salts, acid addition salts or hydrates thereof.

DETAILED DESCRIPTION OF THE INVENTION

In the present invention, all isomers are included unless otherwise noted. For instance, alkyl group, alkoxyl group, alkylene group, alkenylne group and alkynylene group include straight and branched ones, and the alkenylene group includes E- and Z-body and EZ-mixture based on the double bond. The isomers generated from the asymmetric carbon atoms are also included when there is branched alkyl group, alkoxyl group, alkylene group, alkenylene group or alkynylene group.

In the formula (V), the $C_{1-4}$ alkyl group represented by $R^9$, $R^{10}$, $R^{16}$ and $R^{17}$ means a methyl, ethyl, propyl, and butyl group, and these isomers.

In the formula (V), the $C_{1-10}$ alkyl group represented by $R^{11}$, $R^{12}$ and $R^{13}$ means a methyl, ethyl, propyl, butyl, pentyl, hexyl, heptyl, octyl, nonyl, and decyl group, and these isomers.

In the formula (V), the $C_{1-10}$ alkoxyl group represented by $R^{11}$, $R^{12}$ and $R^{13}$ means a methoxy, ethoxy, propyloxy, butyloxy, pentyloxy, hexyloxy, heptyloxy, octyloxy, nonyloxy, and decyloxy group, and these isomers.

In the formula (V), the $C_{1-4}$ alkyl group substituted by a phenyl group represented by $R^{10}$, $R^{12}$, $R^{13}$, $R^{14}$, $R^{16}$ and $R^{17}$ means a methyl, ethyl, propyl, and butyl group substituted by one phenyl group and these isomers.

In the formula (V), the $C_{2-10}$ alkenyl group having 1 to 3 double bonds represented by $R^{11}$, $R^{12}$ and $R^{13}$ means an ethenyl, propenyl, butenyl, pentenyl, hexenyl, heptenyl, octenyl, nonenyl, decenyl, butadienyl, pentadienyl, hexadienyl, heptadienyl, octadienyl, nonadienyl, decadienyl, hexatrienyl, heptatrienyl, octatrienyl, nonatrienyl, and decatrienyl group, and these isomers.

In the formula (V), the $C_{2-10}$ alkynyl group having 1 to 2 triple bonds represented by $R^{11}$, $R^{12}$ and $R^{13}$ means an ethynyl, propynyl, butynyl, pentynyl, hexynyl, heptynyl, octynyl, nonynyl, decynyl, butadiynyl, pentadiynyl, hexadiynyl, heptadiynyl, octadiynyl, nonadiynyl, and decadiynyl group, and these isomers.

In the formula (V), the $C_{3-7}$ cycloalkyl group represented by $R^{11}$, $R^{12}$ and $R^{13}$ means a cyclopropyl, cyclobutyl, cyclopentyl, cyclohexyl, and cycloheptyl group.

In the formula (V), the $C_{1-8}$ alkylene group represented by $R^{15}$ means a methylene, ethylene, trimethylene, tetramethylene, pentamethylene, hexamethylene, heptamethylene, and octamethylene group, and these isomers.

In the formula (V), the 4–7 membered monocyclic heteroring containing 1 to 2 nitrogen atoms represented by

means a pyrrole, pyrrolidine, imidazole, imidazolidine, pyridine, piperidine, pyrazine, piperazine, and pyrimidine ring, etc.

Although each substance used as the active ingredient in the present invention is well-known, detailed description is given below.

The preferred compounds include guanidinoalphatic acid derivatives represented by the formula (I)

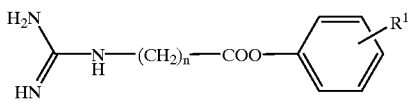
(I)

(in the formula, $R^1$ represents a hydrogen atom, a halogen, a nitro, alkyl, alkoxyl, carboxyl or alkoxycarbonyl group, and n represents an integer of 3 to 6), and nontoxic salts, acid addition salts or hydrates thereof.

The examples of the guanidinoaliphatic acid derivatives represented by the formula (I) which are included in the present invention are the compounds described in JP-B-47-21977, JP-B-50-2494, JP-B-45-33175, JP-B-49-2107, JP-A-48-29732, JP-A-49-24917, JP-A-51-75042 and JP-A-54-76532.

The more preferred compound includes compound 1:

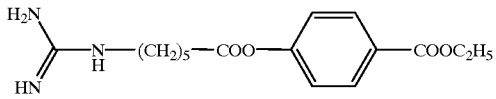

p-ethoxycarbonylphenyl 6-guanidinohexanoate, and nontoxic salts, acid addition salts and hydrates thereof.

The preferred compounds include guanidinobenzoic acid derivatives represented by the formula (II)

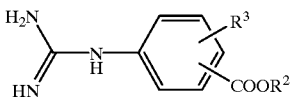
(II)

(in the formula, $R^2$ represents a phenyl group, a naphthyl group, a substituted phenyl group or a substituted naphthyl group, and $R^3$ represents one of various substituting groups), and nontoxic salts, acid addition salts or hydrates thereof.

The examples of the guanidinobenzoic acid derivatives represented by the formula (II) which are encompassed in the present invention are the compounds described in JP-A-48-29732 and 49-24917 (U.S. Pat. No. 3,824,267), JP-A-49-11842, JP-A-50-4038, JP-A-50-69035, JP-A-51-16631, JP-A-52-89640 (U.S. Pat. No. 4,021,472), JP-A-53-15412, JP-A-53-147044, JP-A-54-70241 and 55-55154 (U.S. Pat. No. 4,224,342), JP-A-55-115865 and 55-115863 (U.S. Pat. No. 4,283,418), JP-A-56-34662 (U.S. Pat. No. 4,310,533), JP-A-62-111963 and 63-165357 (EP-A-222608). JP-A-55-100356, JP-A-56-110664, JP-A-57-53454, JP-A-57-142956, JP-A-57-142957, JP-A-57-179146, JP-A-58-41855, JP-A-58-49358, JP-A-61-286361, JP-A-61-286362, JP-A-62-103058, JP-A-62-155253, and GB-A-2083818 and 2095239.

The more preferred compound includes compound 2:

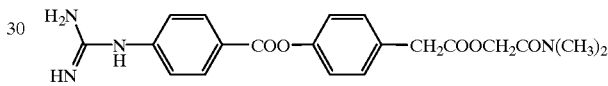

N,N-ddimethylcarbamoylmethyl p-(p-guanidinobenzoyloxy)phenylacetate, compound 3:

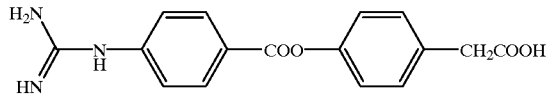

p-(p-guanidinobenzoyloxy)phenylacetic acid, compound 4:

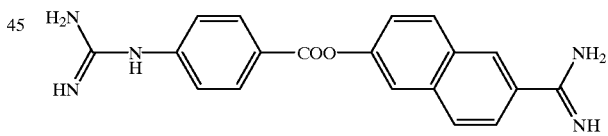

6-amidinonaphtho-2-yl p-guanidinobenzoate, and nontoxic salts, acid addition salts and hydrates thereof.

The preferred compounds include guanidinophenol derivatives represented by the formula (III)

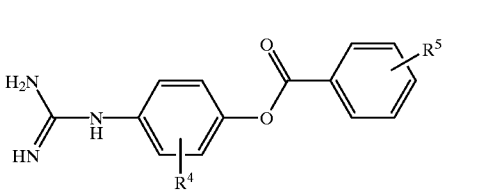
(III)

(in the formula, $R^4$ and $R^5$ represent various substituting groups), and nontoxic salts, acid addition salts or hydrates thereof.

The examples of the guanidinophenol derivatives represented by the formula (III) which are encompassed in the present invention are the compounds described in JP-A-5-286922 and Chem. Pharm. Bull., 32, 4466–4477 (1984), and the compounds represented by the above-mentioned the formula (V).

The more preferred compound includes compound 5:

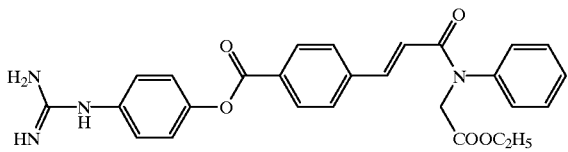

p-(p-guanidinophenoxycarbonyl)cinnamic acid N-phenyl-N-ethoxycarbonylmethylamide, compound 6:

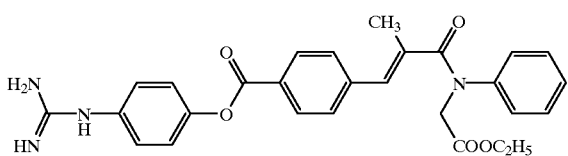

p-(p-guanidinophenoxycarbonyl)-α-methylcinnamic acid N-phenyl-N-ethoxycarbonylmethylamlde, compound 7:

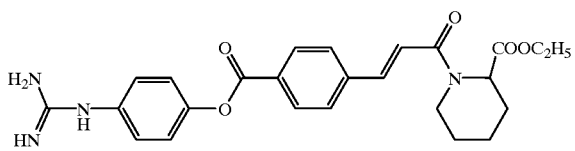

p-(p-guanidinophenoxycarbonyl)cinnamic acid N-(2-ethoxycarbonyl)piperldinylamide, compound 8:

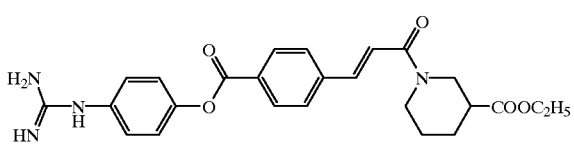

p-(p-guanidinophenoxycarbonyl)cinnamic acid N-(3-ethoxycarbonyl)piperidinylamide, compound 9:

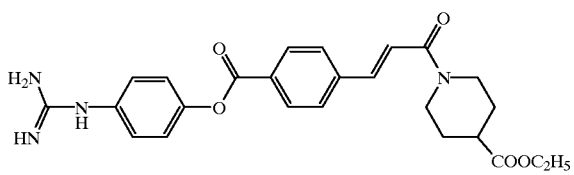

p-(p-guanidinophenoxycarbonyl)cinnamic acid N-(4-ethoxycarbonyl)piperidinylamide, compound 10:

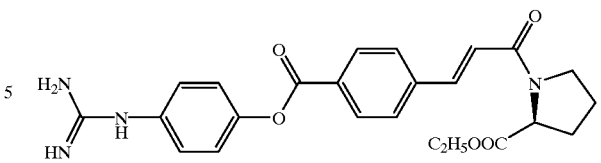

p-(p-guanidinophenoxycarbonyl)cinnamic acid N-(2-(S)-ethoxycarbonyl)pyrrolidinylamide, compound 11:

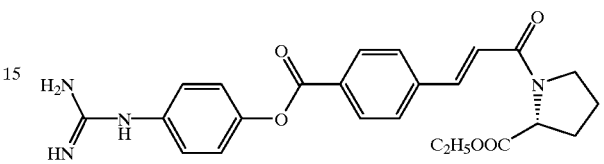

p-(p-guanidinophenoxycarbonyl)cinnamic acid N-(2-(R)-ethoxycarbonyl)pyrrolidinylamide, compound 12:

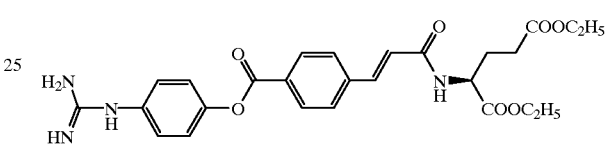

p-(p-guanidinophenoxycarbonyl)cinnamic acid N-(1-(S)-ethoxycarbonyl-3-ethoxycarbonyl)propylamide, compound 13:

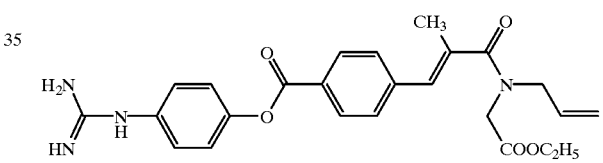

p-(p-guanidinophenoxycarbonyl)-α-methylcinnamic acid N-allyl-N-ethoxycarbonylmethylamide, compound 14:

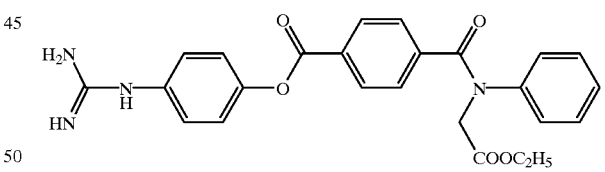

p-(p-guanidinophenoxycarbonyl)benzoic acid N-phenyl-N-ethoxycarbonylmethylamide, compound 15:

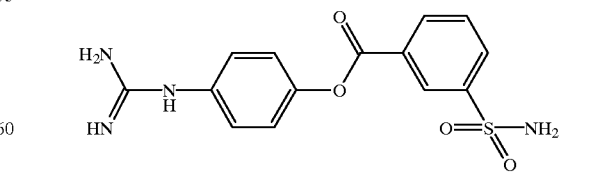

m-(p-guanidinophenoxycarbonyl)benzenesulfonamide, and nontoxic salts, acid addition salts and hydrates thereof.

The preferred compounds include amidinophenol derivatives represented by the formula (IV):

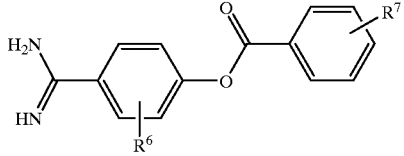

(in the formula, $R^6$ and $R^7$ represent various substituting groups), and nontoxic salt, acid addition salt or hydrate thereof.

The examples of the amidinophenol derivatives represented by the formula (IV) which are included in the present invention are the compounds described in JP-A-58-41855, Japanese Patent Application No. Hei 5-252178 (EP-A-588655), JP-A-7-206801 (EP-A-656349) and Japanese Patent Application No. Hei 7-263599 (EP-A-703216).

The more preferred compound includes compound 16:

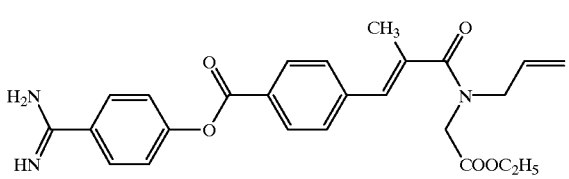

p-(p-amidinophenoxycarbonyl)-α-methylcinnamic acid N-allyl-N-ethoxycarbonylmethylamide, compound 17:

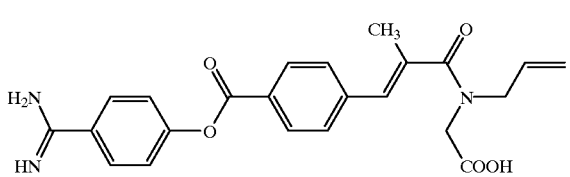

p-(p-amidinophenoxycarbonyl)-α-methylcinnamic acid N-allyl-N-carboxylmethylamide, compound 18:

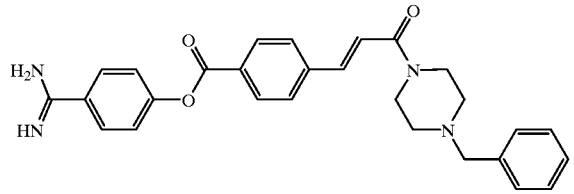

p-(p-amidinophenoxycarbonyl)-α-methylcinnamic acid N-propargyl-N-ethoxycarbonylmethylamide, compound 19:

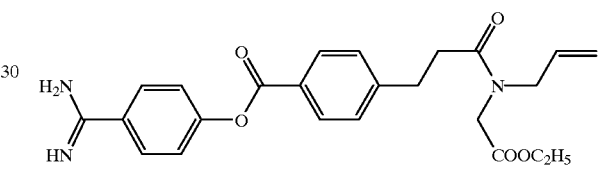

p-(p-amidinophenoxycarbonyl)cinnamic acid N-(4-phenylmethyl)piperadinylamide, compound 20:

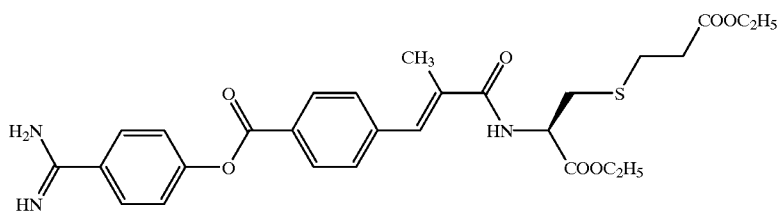

p-(p-amidinophenoxycarbonyl)phenylpropionic acid N-allyl-N-ethoxycarbonylmethylamide, compound 21:

p-(p-amidinophenoxycarbonyl)-α-methylcinnamic acid N-(1-(S)-ethoxycarbonyl-2-ethoxycarbonylethylthio)ethylamide, compound 22:

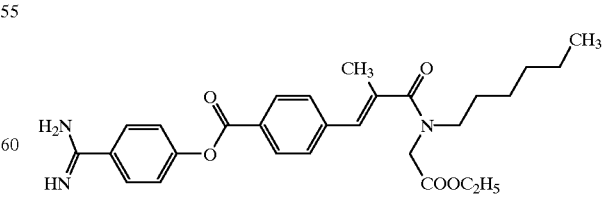

p-(p-amidlnophenoxycarbonyl)-α-methylcinnamic acid N-ethoxycarbonylmethyl-N-hexylamide, compound 23:

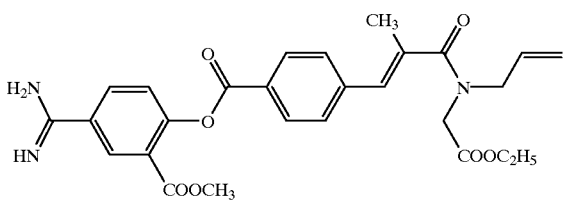

p-(4-amidino-2-methoxycarbonylphenoxycarbonyl)-α-methylcinnamic acid N-allyl-N-ethoxycarbonylmethylamide, compound 24:

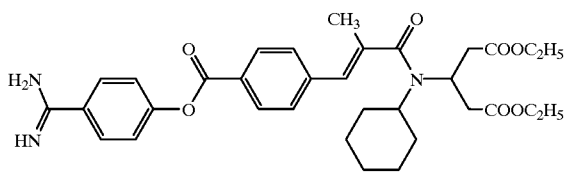

p-(p-amidinophenoxycarbonyl)-α-methylcinnamic acid N-(1,1-bis(ethoxycarbonylmethyl)methyl-N-cyclohexylamide, compound 25:

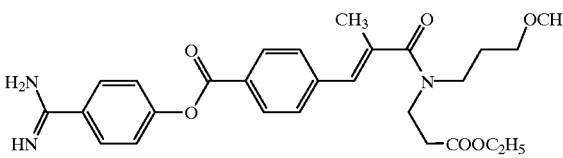

p-(p-amidinophenoxycarbonyl)-α-methylcinnamic acid N-2-ethoxycarbonylethyl-N-3-methoxypropylamide, and nontoxic salts. acid addition salts and hydrates thereof.

In the present invention, each of the active ingredients can be used alone, or two or more kinds of the active ingredients can be incorporated into a preparation.

[Salts]

The compounds of the present invention described in the present specification may be converted into nontoxic salts or acid addition salts by means of the known methods.

The preferable salts are nontoxic and water-soluble ones. Suitable salts include salts of alkali metal (such as potassium and sodium), salts of alkaline-earth metal (such as calcium and magnesium), ammonium salts, and salts of pharmaceutically acceptable organic amine (such as tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, and N-methyl-D-glucamine).

The suitable acid addition salts are nontoxic and water-soluble ones. Suitable acid addition salts include, for instance, inorganic salts such as hydrochloride, hydrobromide, hydrolodide, sulfate, phosphate and nitrate, or organic salts such as acetate, lactate, tartarate, benzoate, citrate, methanesulfonate, ethanesulfonate, benzenesulfonate, toluenesulfonate, isethionate, glucuronate and gluconate, and the preferable ones are methanesulfonate salts.

The compounds of the present invention described in the present specification, or nontoxic salts or acid addition salts thereof may be converted into hydrate by means of the known methods.

The novel guanidinophenol derivatives encompassed in the present invention are the guanidinophenol derivatives represented by the formula (V):

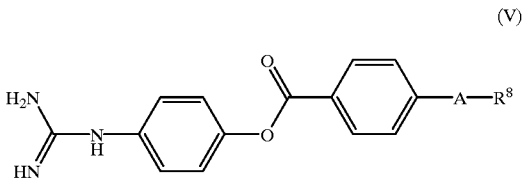

(in the formula, all the symbols represent the same meanings as the above). or nontoxic salts, acid addition salts or hydrates thereof.

The preferred compounds include the above-mentioned compounds 5 to 13, and nontoxic salts, acid addition salts or hydrates thereof.

[Preparation of the Compounds of the Present Invention]

Among the compounds of the present invention, the guanidinoaliphatic acid derivatives represented by the formula (I), the guanidinobenzoic acid derivatives represented by the formula (II), the guanidinophenol derivatives represented by the formula (III) and the amidinophenol derivatives represented by the formula (IV) each can be prepared by the methods described in the above-mentioned specifications.

Among the compounds of the present invention, the guanidinophenol derivatives represented by the formula (V) can be prepared by the following method.

Among the compounds of the present invention represented by the formula (V), the groups represented by $R^{11}$, $R^{12}$, $R^{13}$ and $R^{14}$ in the group $R^8$ of which each represents the group not containing a carboxyl (hereinafter referred to as COOH) group and a t-butoxycarbonyl (hereinafter referred to as COO-t-Bu) group, that is, those represented by the formula (Va):

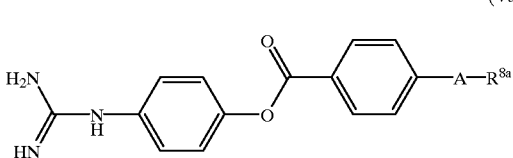

(in the formula, A represents the same meaning as the above, and $R^{8a}$ represents the same meaning as $R^8$ above; provided that $R^{11}$, $R^{12}$, $R^{13}$ and $R^{14}$ in $R^{18}$ each represents the group not containing a COOH group and a COO-t-Bu group) are prepared by allowing a compound represented by the formula (VIa):

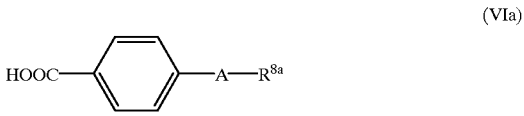

(in the formula, A and $R^{8a}$ represent the same meanings as the above) and p-amidinophenol to esterification reaction.

The esterification reaction is known and exemplified by
(1) a method using acid halide,
(2) a method using mixed acid anhydride,
(3) a method using a condensing agent, etc.

The specific descriptions of these methods are as follows.
(1) The method using acid halide is carried out, for instance, by allowing carboxylic acid to react with acid halide (such as oxalyl chloride, thionyl chloride, etc.) in an inert organic solvent (such as chloroform, methylene chloride, diethyl ether, and tetrahydrofuran) or without solvent at a temperature between −20° C. and the reflux temperature, and allowing the resulting acid halide to react with alcohol in the presence of tertiary amine (such as pyridine, triethylamine, dimethylaniline, and dimethylaminopyridine) in an inert organic solvent (such as chloroform, methylene chloride, diethyl ether, and tetrahydrofuran) at a temperature between 0 and 40° C.

(2) The method using mixed acid anhydride is carried out, for instance, by allowing carboxylic acid to react with acid halide (such as pivaloyl chloride, tosyl chloride, and mesyl chloride) or an acid derivative (such as ethyl chloroformate, isobutyl chloroformate, etc.) in the presence of tertiary amine (such as pyridine, tiethylamine, dimethylaniline, and dimethylaminopyridine) in an inert organic solvent (such as chloroform, methylene chloride, diethyl ether, and tetrahydrofuran) or without solvent at a temperature between 0 and 40° C., and allowing the resulting mixed acid anhydride to react with the corresponding alcohol in an inert organic solvent (such as chloroform, methylene chloride, diethyl ether, and tetrahydrofuran) at a temperature between 0 and 40° C.

(3) The method using a condensing agent (such as 1,3-dicyclohexylcarbodiimide(DCC), 1-ethyl-3-[3-(dimethylamino) propyl]carbodiimide(EDC), 2-chloro-1-methylpyridinium iodide, etc.) is carried out, for instance, by allowing carboxylic acid to react with alcohol in an inert organic solvent (such as chloroform, methylene chloride, dimethylformamide, and diethyl ether) or without solvent, using or without using tertiary amine (such as pyridine, triethylamine, dimethylaniline, and dimethylaminopyridine), and using a condensing agent at a temperature between 0 and 40° C.

These reactions of (1), (2) and (3) are desirably carried out under an inert gas (such as argon and nitrogen) atmosphere under an anhydrous condition.

Among the compounds represented by the formula (V), those of which at least one of the groups represented by $R^{11}$, $R^{12}$ and $R^{13}$ in the group $R^8$ represents a group having a COO-t-Bu group and the other groups each represents a group not having a COOH group, or $R^{14}$ represents a COO-t-Bu group, that is, those represented by the formula (Vb):

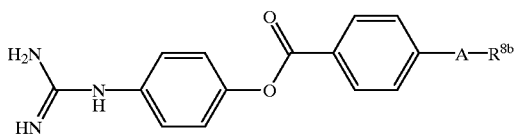

(Vb)

(in the formula, A represents the same meaning as the above, and $R^{8b}$ represents the same meaning as $R^8$ above; provided that at least one of $R^{11}$, $R^{12}$ and $R^{13}$ in $R^8$ represents a group having a COO-t-Bu group and the others each represents a group not having a COOH group or $R^{14}$ represents a COO-t-Bu group) are prepared by allowing a compound represented by the formula (VIb):

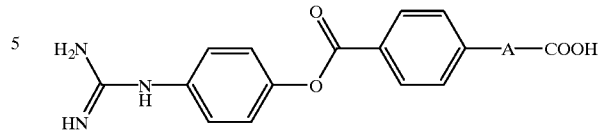

(VIb)

(in the formula, all the symbols represent the same meanings as the above) and a compound represented by the formula (VIb):

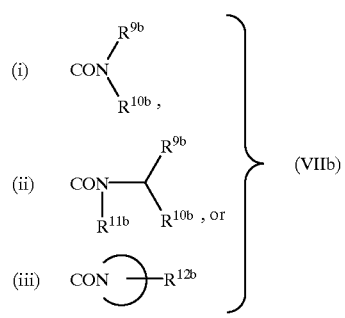

(VIIb)

(in the formulae, $R^{11b}$, $R^{12b}$, $R^{13b}$ and $R^{14b}$ each represents the same meaning as $R^{11}$, $R^{12}$, $R^{13}$ and $R^{14}$, respectively; provided that at least one of $R^{11b}$, $R^{12b}$ and $R^{13b}$ represents a group having a COO-t-Bu group, and the other groups each represents a group not having a COOH group, or $R^{14b}$ represents a COO-t-Bu group) to amidation reaction. This amidation reaction is performed in the same way as the above-mentioned methods for esterification (provided that the amine of formula (VIIb) is used instead of the amidinophenol).

Among the compounds represented by the formula (V), those of which at least one of the groups represented by $R^{11}$, $R^{12}$ and $R^{13}$ in the group $R^8$ represents a group having a COOH group and the other groups each represents a group not having a COO-t-Bu group, or $R^{14}$ represents a COOH group, that is, those represented by the formula (Vc):

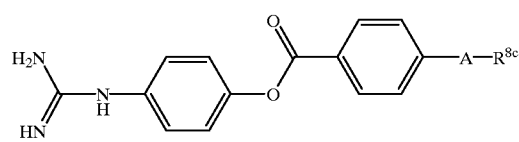

(Vc)

(in the formula, A represents the same meaning as the above, and $R^{8c}$ represents the same meaning as $R^8$ above; provided that at least one of $R^{11}$, $R^{12}$ and $R^{13}$ in $R^8$ represents a group containing a COOH group and the others each represents a group not containing a COO-t-Bu group, or $R^{14}$ represents a COOH group) are prepared by hydrolyzing the COO-t-Bu group of the compounds represented by the formula (Vb) which is prepared by the above-mentioned method.

The hydrolysis of the t-butyl ester group is performed, for instance, in organic acid (such as trifluoroacetic acid) or inorganic acid (such as hydrochloric acid) or a mixture thereof in an inert organic solvent (such as methylene chloride, chloroform, methanol, dioxane, ethyl acetate, and anisole) at a temperature between 0 and 90° C.

The compounds represented by the formulae (VIa) and (VIb) can be prepared by the known methods, the methods described in Japanese Patent Application No. Hei 5-252178 (EP-A-588655), and the similar methods as those described in Japanese Patent Application No. Hei 5-252178 (EP-A-588655).

In each reaction in the present specification, the reaction product can be purified by common purification means, for instance, distillation under normal or reduced pressure, high performance liquid chromatography using silica gel or magnesium silicate, thin layer chromatography, or column chromatography or washing, recrystallization, etc. Purification may be performed after each reaction or after some reactions.

The other starting materials and each reagent are known of themselves or can be prepared by the known methods.

Industrial Applicability

[Effect of the Invention]

As described above, the tryptase inhibitors are thought to be useful for prevention and/or treatment of asthma, pulmonary fibrosis, interstitial pneumonitis, nephritis, hepatic fibrosis, hepatitis, cirrhosis, scleroderma, psoriasis, atopic dermatitis, chronic rheumatism, influenza, Crohn's disease, inflammatory intestinal diseases, ulcerative colitis, nasal allergy, atherosclerosis, etc. Accordingly, the compounds of the present invention represented by the formulae (I), (II), (III) and (IV) which have tryptase inhibitory activity can be used in animals including human, especially in human, as agents for prevention and/or treatment of asthma, pulmonary fibrosis, interstitial pneumonitis, nephritis, hepatic fibrosis, hepatitis, cirrhosis, scleroderma, psoriasis, atopic dermatitis, chronic rheumatism, influenza, Crohn's disease, inflammatory intestinal diseases, ulcerative colitis, nasal allergy, atherosclerosis, etc.

Moreover, the compounds of the present invention represented by the formula (V) are useful for prevention and/or treatment of diseases inhibiting the antagonism of a variety of proteinases (e.g., trypsin, plasmin, thrombin and kallikrein), phospholipase $A_2$ ($PLA_2$) and/or leukotriene $B_4$ ($LTB_4$) other than inhibiting tryptase (e.g., chronic rheumatism, inflammatory intestinal diseases, psoriasis, stomach diseases induced by non-steroidal anti-inflammatory drugs, adult respiratory distress syndrome, myocardial infarction, allergic rhinitis, hemodialysis-inducing neutropenia, late asthma, various inflammatory diseases, allergic diseases, disseminated intravascular coagulation, pancreatitis, severe stages thereof and multiple organ failure).

[Toxicity]

Extremely low toxicity has been confirmed in each of the active ingredients and nontoxic salts and nontoxic acid addition salts thereof encompassed in the present invention. For instance, the $LD_{50}$ of methanesulfonate of compound 16 was 117 mg/kg when intravenously administered to male mice. Accordingly, any of the active substances encompassed in the present invention can be considered to be adequately safe and suitable for use as pharmaceuticals.

[Application to Pharmaceuticals]

The substances described in the present invention are usually administered systemically or locally, orally or parenterally when used for the above-mentioned purpose.

The dosage, however, depends upon the age, body weight, symptom, therapeutic effect, administering way, treatment time, etc., normally, oral administration with the dosage ranging between 1 and 1000 mg an adult is made once to a few times a day, or parenteral administration (preferably intravenous administration) with the dosage ranging between 1 and 100 mg an adult is made once to a few times a day, or continuous administration is intravenously made for 1 to 24 hours a day.

As described above, the dosage alters depending upon the various conditions, and therefore, less dosage than the above may be adequate or more may be necessary.

The compounds of the present invention are administered as solid compositions, liquid compositions and the other compositions for oral administration, and as injections, external preparations, suppositories, etc. for parenteral administration.

The solid compositions for oral administration include tablets, pills, capsules, powders, granules, etc.

The capsules include hard capsules and soft ones.

In such solid compositions, one or more active substances are mixed with at least one inert diluent, e.g., lactose, mannitol, mannite, glucose, hydroxypropylcellulose, microcrystalline cellulose, starch, polyvinyl pyrrolidone and magnesium metasilicate aluminate. The compositions may contain additives except the inert diluent, e.g., tablet lubricants such as magnesium stearate, disintegrants such as fibrous calcium glycolate, and solution adjuvant such as glutamic acid and aspartic acid, in accordance with the conventional way. The tablets and pills may be coated, if necessary, with film of gastrically soluble or enteric substances such as white sugar, gelatin, hydroxypropylcellulose and hydroxypropylmethyl-cellulose phthalate, or with two or more layers. Additionally, capsules of absorbable substances such as gelatin are also included.

The liquid compositions for oral administration include pharmaceutically acceptable emulsions, solutions, syrups, elixirs, etc. In such liquid compositions, one or more active substances are contained ininert diluents generally used (e.g. purified water and ethanol). These compositions may contain adjuvants such as penetrants and suspending agents, sweetening agents, flavoring agents and antiseptics in addition to the inert diluents.

The other compositions for oral administration include sprays that contain one or more active substances and are formulated by the known methods in themselves. These compositions may contain stabilizers to add stability and isotonicity such as sodium hydrogensulfite, and tonicity agents such as sodium chloride, sodium citrate or citric acid. Methods of preparing sprays are described in detail in, e.g., U.S. Pat. Nos. 2,868,691 and 3,095,355.

The injections for parenteral administration according to the present invention include sterile aqueous or nonaqueous solutions, suspensions and emulsions. The aqueous solution and suspensions include, e.g., distilled water for injection and physiological saline. The nonaqueous solutions and suspensions are exemplified by propylene glycol, polyethylene glycol, vegetable oil such as olive oil, alcohol such as ethanol, POLYSORBATE 80 (registered trademark). These compositions may further contain additives such as antiseptics, penetrants, emulsifiers, dispersers, stabilizers, solution adjuvants (e.g., glutamic acid and aspartic acid). These are sterilized by filtration through bacterial filter, addition of bactericide or irradiation. These may be prepared as sterile solid compositions and used with dissolving in sterilized or sterile distilled water for injection or other solvents at use.

The other compositions for parenteral administration include external solutions, ointments, endermic liniments, suppositories for rectal administration and pessaries for vaginal administration which contain one or more active substances and are formulated by the conventional methods.

BEST MODE FOR CARRYING OUT THE INVENTION

The present invention is described in detail in Reference Examples and Examples below. However, the present invention is not limited thereto.

In separation by chromatography, the solvent in the parenthesis shows the eluent or developer used and the ratio means that by volume.

EXAMPLE 1(1)

Tryptase Inhibitory Activity

Tryptase was purified from the human lungs in accordance with the method of T. J. Smithetal. described in J. Biol. Chem., 259, 11046 (1984). The enzyme purified in the concentration of 25.7 U/ml was diluted 10 times with 100 mM Tris/hydrochloride buffer (pH 7.5) at use. The enzyme solution prepared above (5 μl) was mixed with 100 mM Tris/hydrochloride buffer (pH 7.5, 500 μl) and the aqueous solution of the subject compound in various concentrations or water (5 μl), and the resulting mixture was incubated at 37° C. for 5 minutes. To the reaction mixture was added 20 mM Boc-Phe-Ser-Arg-MCA (2.5 μl), and elevation in fluorescence for a minute was determined at Ex=370 nm, Em=460 nm. The elevation in fluorescence in the absence of the subject compound was defined as 100% to obtain the percentage (%) in the existence of the sample compound and calculate the value of $IC_{50}$. Table 1 shows the result.

TABLE 1

| Compound | $IC_{50}$ (nM) |
|---|---|
| Methanesulfonate of compound 1 | 30.0 |
| Methanesulfonate of compound 2 | 4.33 |
| Methanesulfonate of compound 3 | 52.9 |
| Acetate of compound 13 [Example 2(1)] | 5.00 |
| Methanesulfonate of compound 14 | 11.2 |
| Methanesulfonate of compound 15 | 192 |
| Methanesulfonate of compound 16 | 1.4 |
| Methanesulfonate of compound 17 | 12.6 |
| Acetate of compound 18 | 2.39 |
| Hydrochloride of compound 19-2 | 0.21 |
| Acetate of compound 20 | 6.83 |
| Hydrochloride of compound 21 | 1.29 |
| Acetate of compound 22 | 0.24 |
| Acetate of compound 23 | 0.46 |
| Acetate of compound 24 | 1.14 |
| Hydrochloride of compound 25 | 1.38 |

EXAMPLE 1(2)

$PLA_2$ Inhibitory Activity

A reaction mixture was prepared which contained 50 mM Tris/hydrochloride buffer (pH 7.5, 874 μl: 100 mM sodium chloride and 1 mM EDTA contained), 1 M calcium chloride (6 μl), 1% bovine serum albumin (10 μl) and 2.5 mM 10PY-PC (10 μl). To the reaction mixture were added the subject compound in various concentrations or water (50 μl) and a 10 mU/ml $PLA_2$ (derived from pig pancreas) solution (50 μl), and the intensity of fluorescence was determined at Ex=345 nm and Em=396 nm. The intensity of fluorescence in the absence of the subject compound was defined as 100% to obtain the percentage (%) In the existence of the sample compound and calculate the value of $IC_{50}$. Table 2 shows the result.

TABLE 2

| Compound | $IC_{50}$ (μM) |
|---|---|
| Hydrochloride of compound 5 [Example 2(2)] | 8.0 |
| Hydrochloride of compound 6 [Example 2] | 5.0 |

EXAMPLE 1(3)

Trypsin Inhibitory Activity

To 0.2 M HEPES/sodium hydroxide buffer (pH 8.0, 100 μl) and distilled water (640 μl) were added the subject compound in various concentrations or water (10 μl) and a 80 mU/ml trypsin (derived from bovine pancreas) solution (50 μl), and the resulting mixture was allowed to preincubation at 30° C. for a minute. To the resulting reaction mixture, 2.5 mM BAPNA (200 μl) was added, incubation was made at 30° C., and the absorbance at 405 nm was determined. The absorbance in the absence of the subject compound was defined as 100% to obtain the percentage (%) in the existence of the sample compound and calculate the value of $IC_{50}$. Table 3 shows the result.

TABLE 3

| Compound | $IC_{50}$ (μM) |
|---|---|
| Hydrochloride of compound 6 [Example 2] | 0.11 |
| Acetate of compound 7 [Example 2(3)] | 0.18 |
| Acetate of compound 10 [Example 2(6)] | 0.18 |
| Acetate of compound 13 [Example 2(1)] | 0.16 |

EXAMPLE 1(4)

Inhibition of Linkage between $^3H$-$LTB_4$ and Human Polymorphonuclear Leukocyte (PMN)

To a test tube of polypropylene were added 0.049 ml of Hanks balanced salt solution (HBSS). 0.001 ml of the subject compound and 0.05 ml of $^3H$-$LTB_4$ (4 nM) to mix, the reaction was initiated by addition of 0.1 ml of the cell suspension previously well-suspended ($1.6 \times 10^6$ cells/ml), and incubation was made at 0 ° C. for minutes. The reaction was terminated by addition of 2.5 ml of HBSS cooled with ice, the reaction mixture was allowed to suction filtration through Whatman GF/C glass filter with the Brandel cell collector (REANDEL, M-24R) to recover PMN. The filter recovered was washed twice with 2.5 ml of the PBS(−) solution cooled with ice to remove the labeling ligand not linked. The filter was placed in a vial and 8 ml of ACS II cocktail (Amersham) was added to equilibrate. The radiation activity was determined with the liquid scintillation counter (Aloka, LSC-5100).

The amount of $^3H$-$LTB_4$ specifically linked with the receptor was obtained as the value of the difference between the total linkage amount and the nonspecific linkage amount. The nonspecific linkage amount was obtained as the $^3H$-$LTB_4$ linkage amount when adding $LTB_4$ not labeled (1.5 μM) instead of the subject compound.

The inhibitory effect of the subject compound was obtained by the following formula.

Inhibition ratio (%)=100−(B1/B0×100)

B1: The specific linkage amount of $^3H$-$LTB_4$ in the existence of the subject compound
B0: The specific linkage amount of $^3H$-$LTB_4$ in the absence of the subject compound

EXAMPLE 1(5)

Effect on Bleomycin-induced Rat Pulmonary Fibrosis

Under anesthetization with pentobarbital, bleomycin hydrochloride (0.9 mg/0.3 ml) was given to rats by endotracheal administration to induce impairment. The lungs were taken out 15 days after inducing, the effect on pulmonary fibrogenesis was evaluated using the pulmonary hydroxypurine content as the indication. The aqueous solution of the subject compound In concentration of 10 mg/kg was repeatedly given by oral administeration once a day for 14 days, initially administered 10 hours after the administration of bleomycin. Table 4 shows the result.

TABLE 4

| | Amount of pulmonary Hydroxypurine (μg/lung) | Inhibition ratio(%) |
|---|---|---|
| Normal group | 2.676 ± 0.298 | — |
| Control group | 4.526 ± 0.439 | — |
| Methanesulfonate of compound 17 | 3.774 ± 0.504 | 40.6 |

EXAMPLE 1(6)

Effect on Carbon Tetrachloride-induced Rat Chronic Hepatopathy

Carbon tetrachloride (1.5 mg/kg) was repeatedly given to rats by subctaneous administration twice a week for 12 weeks to induce impairment. The liver was taken out 12 weeks after inducing, the effect on hepatic fibrogenesis was evaluated using the hepatic hydroxypurine content as the indication. The aqueous solution of the subject compound in concentration of 3 mg/kg was repeatedly given by oral administeration once a day for 8 weeks, initially administered 5 weeks after the administration of carbon tetrachloride. Table 5 shows the result.

TABLE 5

| | Amount of hepatic Hydroxypurine (μg/liver) | Inhibition ratio(%) |
|---|---|---|
| Normal group | 489.8 ± 170.1 | — |
| Control group | 1461.1 ± 1067.9 | — |
| Methanesulfonate of compound 16 | 896.5 ± 686.7 | 58.1 |

In the experiments above, Boc-Phe-Ser-Arg-MCA represents t-butoxycarbonyl-phenylalanine-serine-arginine-methyl-coumarinamide, 10PY-PC represents 3'-palmitoyl-2-(1-pyrenedecanoyl)-L-α-phosphatidyl choline, HEPES represents 4-(2-hydroxyethyl)-1-piperazine-ethanesulfonic acid, and BAPNA represents α-N-benzoyl-DL-arginine-p-nitroanilide hydrochloride.

REFERENCE EXAMPLE 1

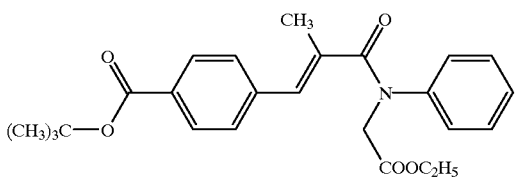

To the dimethylformamide (80 ml) solution of p-(t-butoxycarbonyl)-α-methylcinnamic acid [described in Reference Example 7 of Japanese Patent Application No. Hei 5-252178 (EP-A-588655)] (8.2 g) were added N-(ethoxycarbonylmethyl)phenylamine (5.4 g) and 1-ethyl-3-[3-(diethylamino)propyl]carboduimide (hereinafter abbreviated as EDCI) (10.18 g). The reaction mixture was stirred at room temperature for 3 days. The reaction mixture was poured into ice-water and extracted with a mixed solvent of hexane:ethyl acetate=1:1. The extract was washed in turn with 1 N aqueous hydrochloric acid, 1N aqueous sodium hydroxide and saturated aqueous sodium chloride, dried with magnesium sulfate anhydride, and concentrated. The resulting residue was purified by silica gel column chromatography (hexane:ethyl acetate=4:1 to 2:1) to obtain the titled compound having the following value of property (4.34 g).

TLC: Rf 0.42 (hexane:ethyl acetate=3:1).

REFERENCE EXAMPLE 2

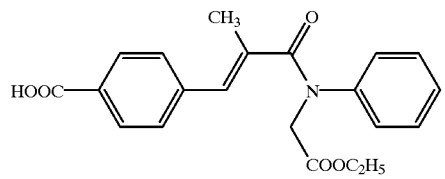

To the anisole (30 ml) solution of the compound prepared in Reference Eeample 1 (4.34 g) was added trifluoroacetic acid (20 ml). The reaction mixture was stirred at room temperature for 5 hours. After condensing the reaction mixture, isopropyl ether was added to the residue, and the precipitate was separated by filitration, washed with isopropyl ether and dried to obtain the titled compound having the following value of property (3.1 g).

TLC: Rf 0.30 (hexane:ethyl acetate:acetlc acid=12:4:1).

EXAMPLE 2 p-(p-Guanidinophenoxycarbony) -α-methylcinnamic Acid N-phenyl-N-ethoxycarbonylmethylamide Hydrochloride (hydrochloride of compound 6)

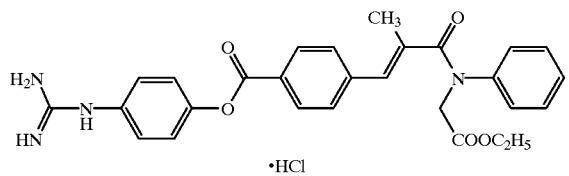

To the pyridine (40 ml) solution of the compound prepared in Reference Example 2 were added p-guanidinophenol hydrochloride (1.15 g) and 1,3-dicyclohexylcarbodiimide (1.26 g). The reaction mixture was stirred at room temperature for 3 days and filtered, and the filtrate was concentrated. The residue was purified by silica gel column chromatography (chloroform:methanol:acetic acid=30:2:1 to 20:2:1). The resulting compound was dissolved in dioxane (30 ml) and 1 N aqueous hydrochloric acid (50 ml) and heated to 30° C. The mixture was concentrated to remove water, ether was added to the resulting residue, and the precipitate was separated by filtration and dried to obtain the compound of the present invention (1.11 g) as white powder having the folloing value of property.

TLC: Rf 0.43 (chloroform:methanol:acetic acid=15:2:1); IR(KBr): ν 3371, 1736, 1636, 1585, 1510, 1376, 1268, 1201, 1073, 1015, 889, 770, 700, 519 cm$^{-1}$; NMR(CD$_3$OD): δ 8.10(2H,d,J=8.0 Hz), 7.48–7.28(9H,m), 7.25 (2H,d,J=8.0 Hz),6.68(1H,brs), 4.55(2H,s), 4.22(2H,q,J=7.5 Hz), 1.90 (3H,d,J=1 Hz), 1.30(3H,t,J=7.5 Hz).

EXAMPLES 2(1) to 2(8)

Using p-(t-butoxycarbonyl)-α-methylcinnamic acid and p-(p-methoxybenzyloxycarbonyl)cinnamic acid instead thereof [described in Reference Example 8 of Japanese Patent Application No. Hei 5-252178 (EP-A-588655)], and N-(ethoxycarbonylmethyl)phenylamine and the corresponding amine instead of it, the similar operations as a series of reaction of Reference Example 1→Reference Example 2→Example 2 were carried out, and the conventional method was performed to convert into the corresponding acid addition salt to obtain the compounds of the present invention having the following values of property.

EXAMPLE 2(1)

p-(p-Guanidinophenoxycarbonyl)-α-methylcinnamic Acid N-allyl-N-ethoxycarbonylmethylamide Acetate (acetate of compound 13)

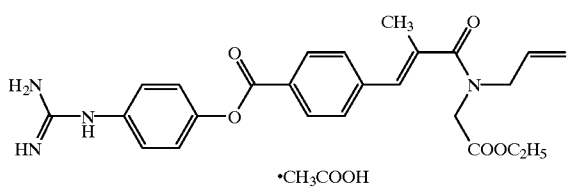

TLC: Rf 0.47 (chloroform:methanol:acetic acid=10:2:1); IR(KBr): ν3373, 1737, 1679, 1610, 1510, 1411, 1268, 1201, 1073, 1016, 888, 762, 659, 520 cm$^{-1}$; NMR(CD$_3$OD): δ 8.20(2H,d,J=9.0 Hz), 7.57(2H.d,J=9.0 Hz), 7.38 (4H,s), 6.73 and 6.66(1H,m), 5.89(1H,m), 5.33–5.27(2H,m), 4.22 (2H, q,J=7.0 Hz), 4.11(4H,m), 2.13(3H,s), 1.94(3H,s), 1.28 (3H, t,J=7.0 Hz).

EXAMPLE 2(2)

p-(p-Guanidinophenoxycarbonyl)cinnamic Acid N-phenyl-N-ethoxycarbonylmethylamide Hydrochloride (hydrochloride of compound 5)

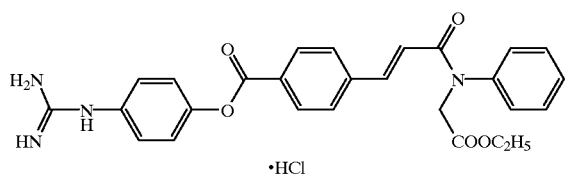

TLC: Rf 0.53 (chloroform:methanol:acetic acid=10:2:1); IR(KBr): ν 3332, 2362, 1736, 1656, 1509, 1262, 1198, 1074, 1017, 766, 702 cm$^{-1}$; NMR(CD$_3$OD): δ 8.15(2H,d,J=8.0 Hz), 7.68(1H,d,J=15.0 Hz), 7.60–7.28(11H,m), 6.58(1H,d, J=15.0 Hz), 4.52(2H,s), 4.22(2H,q, J=7.5 Hz), 1.25(3H,t,J= 7.5 Hz).

EXAMPLE 2(3)

p-(p-Guanidinophenoxycarbonyl)cinnamic Acid N-(2-ethoxcarbonyl)piperidlnylamide acetate (acetate of compound 7)

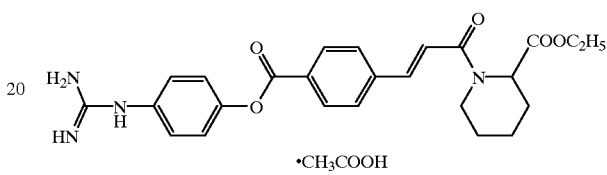

TLC: Rf 0.23 (chloroform:methanol:acetic acid=10:1:1); IR(KBr): ν 3338, 2943, 1735, 1678, 1646, 1590, 1446, 1412, 1268, 1203, 1181, 1161, 1076, 1027, 765, 522 cm$^{-1}$; NMR (CD$_3$OD): δ 8.20(2H,d,J=8.0 Hz), 7.83(2H,d,J=8.0 Hz), 7.63 (1H,d,J=15.0 Hz), 7.36(1H,d,J=15.0 Hz), 7.38(4H,s), 5.34(0.7H, br.s), 5.17(0.3H,br.s), 4.58–4.51(0.5H,m), 4.26–4.19(0.5H,m), 4.23(2H,q,J=7.0 Hz), 3.43–3.31(1H,m), 2.88–2.70(0.3H,m), 2.50–2.25(1H,m), 1.90–1.35(4.7H,m), 1.29(3H,t,J=7.0 Hz).

EXAMPLE 2(4)

p-(p-Guanidinophenoxycarbonyl)cinnamic Acid N-(3-ethoxycarbonyl)piperidinylamide Acetate (acetate of compound 8)

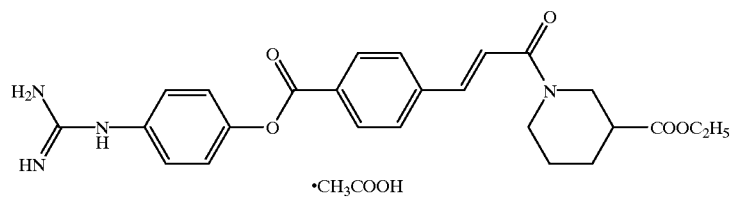

TLC: Rf 0.22 (chloroform:methanol:acetic acid=10:1::1); IR(KBr): ν 3372, 1735, 1647, 1610, 1510, 1445, 1412, 1266, 1200, 1180, 1073, 1015, 766, 520 cm$^{-1}$; NMR(CD$_3$OD): δ 8.20(2H,d,J=8.0 Hz), 7.82(2H,d,J=8.0 Hz), 7.61 (1H,d,J=15.5 Hz), 7.34(1H,d,J=15.5 Hz), 7.38(4H,s), 4.60–4.40 (0.5H,m), 4.22–4.00(2.5H,m), 4.00–3.85(1H,m), 3.80–3.55 (1H, m), 3.30–3.10(1H,m), 2.75–2.46(1H,m), 2.20–1.45 (4H,m), 1.27–1.18(3H,m).

EXAMPLE 2(5)

p-(p-Guanidinophenoxycarbonyl)cinnamic Acid N-(4-ethoxycarbonyl)piperidinylamide Acetate (acetate of compound 9)

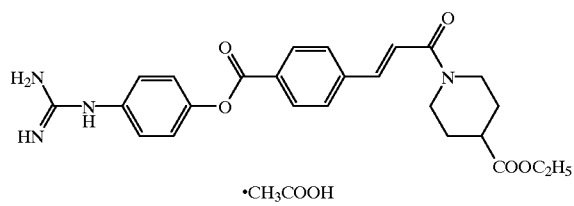

TLC: Rf 0.20 (chlorofoxm:methanol:acetic acid=10:1:1); IR(KBr): ν 3349, 1734, 1685, 1646, 1593, 1510, 1446, 1412, 1318, 1268, 1199, 1180, 1074, 1042, 1016, 766, 669, 520 cm$_{-1}$; NMR(CD$_3$OD): δ 8.20(2H,d,J=8.5 Hz), 7.82(2H,d,J=8.5 Hz), 7.62 (1H,d,J=15.5 Hz), 7.35(1H,d,J=15.5 Hz), 7.37(4H,s), 4.50–4.35 (1H,m), 4.30–4.15(1H,m), 4.15(2H,q, J=7.0 Hz), 3.45–3.25(1H,m), 3.14–2.90(1H,m), 2.80–2.60 (1H,m), 2.10–1.90(2H, 1.80–1.52 (2H,m), 1.26(3H,t,J=7.0 Hz).

EXAMPLE 2(6)

p-(p-Guanidinophenoxycarbonyl)cinnamic Acid N-(2-(S)-ethoxycarbonyl)pyrrolidinylamide Acetate (acetate of compound 10)

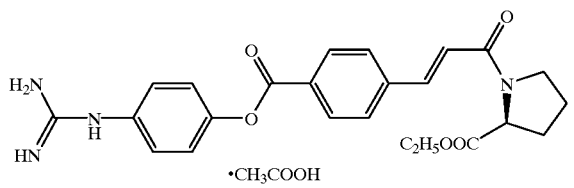

TLC: Rf 0.28 (chloroform:methanol:acetic acid=10:2:1); IR(KBr): ν 3387, 2981, 1737, 1677, 1650, 1610, 1590, 1510, 1439, 1409, 1271, 1200, 1181, 1073, 1015 cm$^{-1}$, NMR (CD$_3$OD): δ 8.20(2H,d,J=8 Hz). 7.85 and 7.75(2H,d,J=8 Hz), 7.65(1H,d,J=15 Hz), 7.40(4H,s), 7.15 and 6.90(1H,d, J=15 Hz), 4.55(1H,m), 4.20(2H,q,J=7.5 Hz), 3.85(2H,m), 2.30(1H,m), 2.20–2.00 (3H,m), 2.00(3H,s), 1.30(3H,t,J=7.5 Hz).

EXAMPLE 2(7)

p-(p-Guanidinophenoxycarbonyl)cinnamic Acid N-(2-(R)-ethoxycarbonyl)pyrrolidinylamide Acetate (acetate of compound 11)

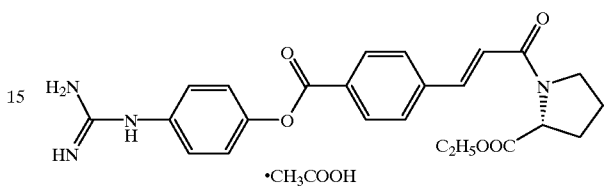

TLC: Rf 0.28 (chlorofonm:methanol:acetic acid=10:2:1); IR(KBr): ν 3410, 1736, 1649, 1611, 1510, 1439, 1409, 1273, 1199, 1073, 1015 cm$_{-1}$; NMR(CD$_3$OD): δ 8.20(2H,d,J=8 Hz), 7.85 and 7.75(2H,d,J=8 Hz), 7.65(1H,d,J15 Hz), 7.40 (4H,s), 7.15 and 6.90(1H,d,J=15 Hz), 4.55(1H,m), 4.20(2H, q,J=7.5 Hz), 3.85(2H,m), 2.30(1H,m), 2.20–2.00 (3H,m), 2.00(3H,s, CH$_3$COOH), 1.30(3H,t,J=7.5 Hz).

EXAMPLE 2(8)

p-(p-Guanidinophenoxycarbonyl)cinnamic Acid N-(1-(S)-ethoxycarbonyl-3-ethoxycarbonyl) propylamide Hydrochloride (hydrochloride of compound 12)

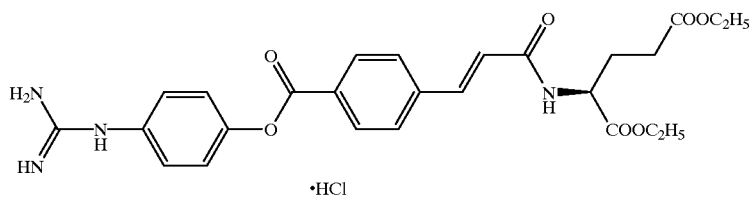

TLC: Rf 0.28 (chloroform:methanol:acetic acid=15:2:1); IR(KBr): ν 3246, 1729, 1662, 1634, 1546, 1508, 1276, 1204, 1079, 1017, 769 cm$^{-1}$; NMR(CD$_3$OD): δ 8.20(2H,d,J=8.5 Hz), 7.78(2H,d,J=8.5 Hz), 7.61 (1H,d,J=15 Hz), 7.40(4H,s), 6.82(1H,d,J=15 Hz), 4.58(1H,dd, J=5.0,8.0 Hz), 4.20(2H,q, J=8.0 Hz), 4.15(2H,q,J=8.0 Hz), 2.45 (2H,t,J=8.0 Hz), 2.35–1.90(2H,m), 1.27(3H,t,J=8.0 Hz), 1.24(3H, t,J=8.0 Hz).

FORMULATION EXAMPLE

FORMULATION EXAMPLE 1

The following ingredients were mixed by the conventional method and tableted to obtain 100 tablets containing 50 mg of the active ingredient per tablet.

| | |
|---|---|
| p-(p-Amidinophenoxycarbonyl)-α-methylcinnamic acid N-ethoxycarbonylmethyl-N-allylamide methanesulfonate (methane-sulfonate of compound 16) | 5.0 g |
| Carboxymethylcellulose calcium (disintegrating agent) | 0.2 g |
| Magnesium stearate (tablet lubricant) | 0.1 g |
| Microcrystalline cellulose | 4.7 g |

FORMULATION EXAMPLE 2

The following ingredients were mixed by the conventional method, the solution was sterilized by the conventional method, each 5 ml was packed into ampules, and the ampules were lyophilized by the conventional method to obtain 100 ampules containing 20 mg of the active ingredient per ampule.

| | |
|---|---|
| p-(p-Amidinophenoxycarbonyl)-α-methylcinnamic acid N-ethoxycarbonylmethyl-N-allylamide methanesulfonate (methane-sulfonate of compound 16) | 2 g |
| Citric anhydride | 200 mg |
| Distilled water | 500 ml |

What is claimed is:

1. A method for the prevention and/or treatment of diseases induced by tryptase, which comprises administering to a patient an effective amount of a guanidinoaliphatic acid derivative represented by the formula (I)

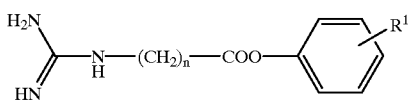

(wherein $R^1$ represents a hydrogen atom, a halogen atom, a nitro group, an alkyl group, an alkoxyl group, a carboxyl group or an alkoxycarbonyl group, and n represents an integer of 3 to 6), a nontoxic salt thereof or an acid addition salt, or a hydrate thereof.

2. A method for the prevention and/or treatment of diseases induced by tryptase, which comprises administering to a patient an effective amount of a guanidinobenzoic acid derivative represented by the formula (II)

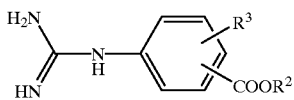

(wherein $R^2$ is

1)

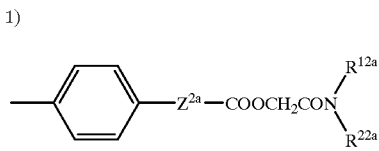

wherein $Z^{2a}$ is methylene, ethylene or vinylene,
$R^{12a}$ and $R^{22a}$ each, independently, is hydrogen or C1–3 alkyl,

2)

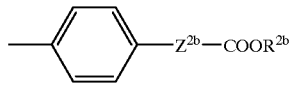

wherein $Z^{2b}$ is methylene, ethylene or vinylene,
$R^{2b}$ is hydrogen or C1–3 alkyl,

3)

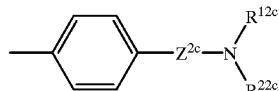

wherein $Z^{2c}$ is $SO_2$ or $Z^{2c'}$—CO,
$Z^{2c'}$ is methylene, ethylene or vinylene,
$R^{12c}$ and $R^{22c}$ each, independently, is hydrogen or C1–3 alkyl,

4)

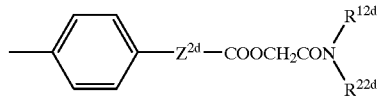

wherein $Z^{2d}$ is single bond, methylene, ethylene or vinylene,
$R^{12d}$ is hydrogen or C1–4 alkyl,
$R^{22d}$ is C4–10 alkyl, C3–8 cycloalkyl, C3–8 cycloalkenyl, C3–8 alkenyl, phenyl or benzyl, or
$NR^{12d}R^{22d}$ represents 4-to 8-membered heterocyclic ring, or

5)

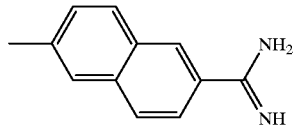

$R^3$ is hydrogen),
a nontoxic salt thereof or an acid addition salt, or a hydrate thereof.

3. A method for the prevention and/or treatment of diseases induced by tryptase, which comprises administering to a patient an effective amount of a guanidinophenol derivative represented by the formula (III)

(III)

(wherein $R^4$ is hydrogen, $R^5$ is:
(i) C1–4 alkyl,
(ii) C1–4 alkoxy,
(iii) —COOR$^{15a}$ (in which R$^{15a}$ is hydrogen or C1–4 alkyl);
(iv) —COR$^{25}$ (in which R$^{25}$ is C1–4 alkyl or phenyl);
(v) —O—A$^5$—COOR$^{35}$ (in which A$^5$ is C1–4 alkylene, R$^{35}$ is hydrogen or C1–4 alkyl);
(vi) —NR$^{45}$R$^{55}$ (in which R$^{45}$ and R$^{55}$ each, independently, is hydrogen or C1–4 alkyl);
(vii) —B$^5$—NR$^{65}$R$^{75}$ (in which B$^5$ is sulfonyl or carbonyl, R$^{65}$ is hydrogen, C1–4 alkyl, phenyl or C7–10 phenylalkyl, R$^{75}$ is hydrogen, C1–4 alkyl, phenyl, C7–10 phenylalkyl or —D$^5$—COOR$^{85}$ (in which D$^5$ is C1–4 alkylene, R$^{85}$ is hydrogen, C1–7 alkyl or C7–10 phenylalkyl); or R$^{65}$ and R$^{75}$ taken together with nitrogen neighboring thereto, is

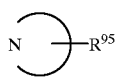

(in which

is 4–7 membered saturated monocyclic heterocyclic ring or fuzed heterocyclic ring with benzene ring, R$^{95}$ is hydorogen or —COOR$^{105}$ (in which R$^{105}$ is hydrogen, C1–4 alkyl or C7–10 phenylalkyl)));

viii)

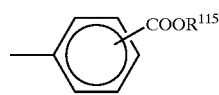

(in which R$^{115}$ is hydrogen, C1–7 alkyl, or 4–14 membered monocyclic or polycyclic alkyl); or ix)

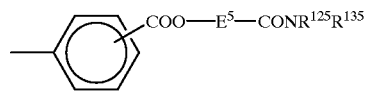

(in which E$^5$ is C1–4 alkylene, R$^{125}$ and R$^{135}$ each, independently, is hydrogen or C1–4 alkyl)), a nontoxic salt thereof or an acid addition salt, or a hydrate thereof.

4. A method for the prevention and/or treatment of diseases induced by tryptase, which comprises administering to a patient an effective amount of a amidinophenol derivative represented by the formula (IV)

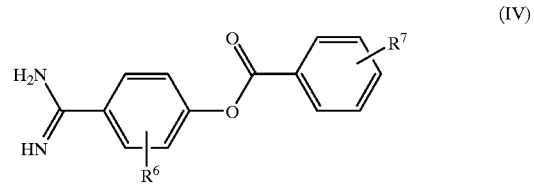

(wherein
(1) R$^6$ is:
(i) hydrogen,
(ii) C1–4 alkyl,
(iii) C1–4 alkoxy,
(iv) C2–5 acyl,
(v) halogen,
(vi) nitro,
(vii) benzoyl or
(viii) COOR$^{46}$ (in which R$^{46}$ is C1–3 alkyl);
R$^7$ is —A$^7$—R$^{37}$
wherein A$^7$ is a bond, C1–4 alkylene or

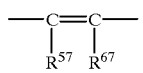

(in which R$^{57}$ and R$^{67}$ each, independently, is hydrogen or C1–4 alkyl);
R$^{37}$ is i)

ii)

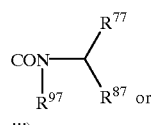 or iii)

(in which R$^{77}$ and R$^{87}$ each, independently, is
(1) hydrogen,
(2) phenyl,
(3) C7–10 phenylalkyl,
(4) phenyl or C7–10 phenylalkyl each of which is substituted by one or two substituents selected from C1–4 alkyl, halogen and R$^{117}$COOR$^{127}$
(in which R$^{117}$ is
(a) a bond,
(b) C1–8 alkylene,
(C) C2–8 alkenylene or
(d) C2–8 alkynylene, and
R$^{127}$ is
(a) hydrogen,
(b) C1–4 alkyl,
(c) C7–10 phenylalkyl, (d) phenyl,
(e) allyl or
(f) propargyl),
(5) C1–10 alkyl,
(6) C2–10 alkenyl having one to three double bonds,
(7) C2–10 alkynyl having one or two triple bonds,
(8) $R^{117a}$—$COX^7R^{127}$
  (in which $R^{117a}$ is
    (a) a bond,
    (b) C1–8 alkylene,
    (c) C2–8 alkylene in which one or two carbon atoms in the main chain are replaced by sulfur, or sulfur and phenylene,
    (d) C2–8 alkenylene,
    (e) C4–8 alkenylene in which one or two carbon atoms in the main chain are replaced by sulfur, or sulfur and phenylene,
    (f) C2–8 alkynylene, or
    (g) C4–8 alkynylene in which one or two carbon atoms in the main chain are replaced by sulfur, or sulfur and phenylene,
  $X^7$ is oxygen or —NH—, and
  $R^{127}$ is the same meaning as hereinbefore defined),
(9) C1–4 alkyl which is substituted by a 7–14 membered, bi- or tri-cyclic hetero ring containing one nitrogen, or
(10) C3–7 cycloalkyl);
$R^{97}$ is
  (1) hydrogen,
  (2) C1–8 alkyl,
  (3) C7–10 phenylalkyl,
  (4) C2–10 alkenyl having one to three double bonds,
  (5) C2–10 alkynyl having one or two triple bonds,
  (6) $R^{117}$—$COOR^{127}$ (in which $R^{117}$ and $R^{127}$ are the same meaning as hereinbefore defined), or
  (7) C3–7 cycloalkyl;

is 4–7 membered, mono-cyclic hetero ring containing one or two nitrogen; $R^{107}$ is
  (1) hydrogen,
  (2) C7–10 phenylalkyl or
  (3) $COOR^{137}$ (in which $R^{137}$ is hydrogen, C1–4 alkyl or C7–10 phenylalkyl));
  with the proviso that
    (i) both $R^{77}$ and $R^{87}$ do not represent hydrogen at the same time, and
    (ii) when at least one group in $R^{77}$, $R^{87}$ and $R^{97}$ represents the group containing t-butyl ester, the other groups do not represent the group containing carboxy;
(2) $R^6$ is
  (i) hydrogen,
  (ii) C1–4 alkyl,
  (iii) C1–4 alkoxy,
  (iv) C2–5 acyl,
  (v) halogen,
  (vi) nitro,
  (vii) benzoyl, or
  (viii) $COOR^{46b}$ (in which $R^{46b}$ is C1–3 alkyl);
$R^7$ is —$A^{7b}$—$R^{37b}$ wherein $A^{7b}$ is bond, C1–4 alkylene, or

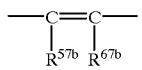

(in which $R^{57b}$ and $R^{67b}$ each, independently, is hydrogen or C1–4 alkyl);
$R^{37b}$ is i)

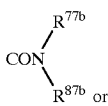

ii)

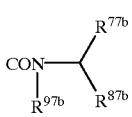

(in which $R^{77b}$ and $R^{87b}$ each, independently, is
  (1) hydrogen,
  (2) phenyl,
  (3) C7–10 phenylalkyl,
  (4) phenyl or C7–10 phenylalkyl each of which is substituted by one or two substituents optionally selected from C1–4 alkyl, halogen and $R^{117b}$—$COOR^{127b}$
(in which $R^{117}$ is
  a bond,
  C1–8 alkylene,
  C2–8 alkenylene, or
  C2–8 alkynylene;
$R^{127b}$ is
  hydrogen,
  C1–4 alkyl,
  C7–10 phenylalkyl,
  phenyl,
  allyl, or
  propargyl),
  (5) C1–10 alkyl,
  (6) C2–10 alkenyl having one to three double bonds,
  (7) C2–10 alkynyl having one or two triple bonds,
  (8) $R^{117ba}$—$COX^{7b}R^{127b}$
(in which $R^{117ba}$ is
  a bond,
  C1–8 alkylene,
  C2–8 alkylene in which one or two carbon atoms in the main chain are replaced by sulfur, or sulfur and phenylene,
  C2–8 alkenylene,
  C4–8 alkenylene in which one or two carbon atoms in the main chain are replaced by sulfur, or sulfur and phenylene,
  C2–8 alkynylene, or
  C4–8 alkynylene in which one or two carbon atoms in the main chain are replaced by sulfur, or sulfur and phenylene,
$X^{7b}$ is oxygen or —NH—, and
$R^{127b}$ has the same meaning as hereinbefore defined),
  (9) C1–4 alkyl which is substituted by a 7–14 membered, bi- or tri-cyclic hetero ring containing one nitrogen,

(10) C3–7 cycloalkyl, or
(11) C1–6 alkyl which is substituted by a C1–4 alkoxy;

$R^{97b}$ is
(1) hydrogen,
(2) C1–8 alkyl,
(3) C7–10 phenylalkyl,
(4) C2–10 alkenyl having one to three double bonds,
(5) C2–10 alkynyl having one or two triple bonds,
(6) $R^{117b}$—$COOR^{127b}$ (in which $R^{117b}$ and $R^{127b}$ are same meaning as hereinbefore defined),
(7) C3–7 cycloalkyl, or
(8) C1–6 alkyl which is substituted by C1–4 alkoxy);

with the proviso that
(i) one of the groups $R^{77b}$, $R^{87b}$ and $R^{97b}$ represents C1–6 alkyl which is substituted by C1–4 alkoxy,
(ii) $R^{77b}$ and $R^{87b}$ do not simultaneously represent hydrogen, and
(iii) when one of $R^{77b}$, $R^{87b}$ and $R^{97b}$ represents at-butoxycarbonyl-containing group,
the other two do not represent carboxy-containing groups; or
(3) $R^6$ is hydrogen, C1–4 alkyl, or C1–4 alkoxy, $R^7$ is —$A_0$—$R^{7c}$—
wherein $A_0$ is a single bond, C1–4 alkylene, -oxy-(C1–4) alkylene-, -thio-(C1–4)alhylene-, C2–8 alkenylene, or C2–8 alkenylene which is substituted by carboxy or by C1–4 alkoxycarbonyl, $R^{7c}$ is a group of the formula:

i)
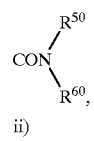

ii)
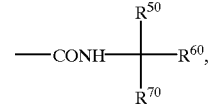

iii)
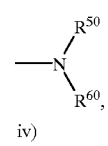

iv)
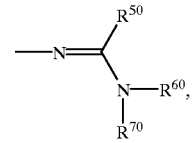

v)
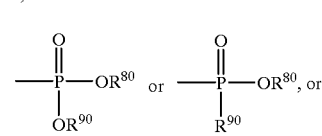

vi)
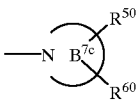

(in which the grouping:

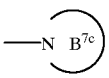

is a 4–10 membered hetero ring containing one or two nitrogen atoms;

$R^{50}$, $R^{60}$ and $R^{70}$ each independently, is
(i) hydrogen,
(ii) C1–8 alkyl,
(iii) C2–8 alkenyl,
(iv) —$COOR^{110}$(in which $R^{110}$ is hydrogen or C1–4 alkyl unsubstituted or substituted by phenyl),
(v) —C1–8 alkylene)-$COOR^{110}$(in which $R^{110}$ has the same meaning as hereinbefore defined),
(vi) —(C2–8 alkenylene)-$COOR^{110}$(in which $R^{110}$ has the same meaning as hereinbefore defined),
(vii) C4–7 cycloalkyl,
(viii) —C1–4 alkylene)-(4–7 membered hetero ring containing one oxygen),
(ix) —C1–4 alkylene)-(4–7 membered hetero ring containing one nitrogen),
(x) phenyl,
(xi) C1–8 alkyl which is substituted by one or two phenyl,
(xii) C1–4 alkylene)-O-benzoyl,
(xiii) —C1–4 alkylene)-CONH—(C1–4 alkylene)-$NR^{120}R^{130}$,
(xiv) —C1–4 alkylene)-COO(C1–4 alkylene)-$NR^{120}R^{130}$,
(xv) —C1–4 alkylene)-COO-amidinophenyl,
(xvi) —(C1–4 alkylene)-CONH-(C1–4 alkyl which is substituted by one or two $COOR^{110}$)(in which $R^{110}$ has the same meaning as hereinbefore defined),
(xvii) C1–4 alkylene)-$CONR^{120}R^{130}$, or
(xviii) —(C1–4)alkoxy(C1–4)alkyl;

$R^{80}$ and $R^{90}$ each independently, is C1–4 alkyl or C1–4 alkylene)-phenyl, $R^{120}$ and $R^{130}$ each independently, is hydrogen, C1–4 alkyl, or C2–8 alkenyl, with the provisos that:
(1) $R^{50}$ and $R^{60}$ in the formulae (i) and (iii), and $R^{50}$, $R^{60}$ and $R^{70}$ in the formulae (ii) and (iv), do not represent hydrogen at the same time,
(2) when at least one substituent in $R^{50}$, $R^{60}$, $R^{70}$ and $A_0$ represent substituent containing —COO-t-Bu, the other groups do not represent groups containing carboxy,
(3) $R^{120}$ and $R^{130}$ do not represent hydrogen at the same time,
(4) when $A_0$ is a single bond, C1–4 alkylene or vinylene which is optionally substituted by one or two C1–4 alkyl, and $R^{7c}$ is the formula(i) as hereinbefore described, then at least one group in $R^{50}$, $R^{60}$ and $R^{70}$ is
(viii) —C1–4 alkylene)-(4–7 membered hetero ring containing one oxygen),
(ix) —C1 -alkylene)-(4–7 membered hetero ring containing one nitrogen), (x) phenyl,
(xi) —(C1–8 alkyl which is substituted by one or two phenyl,
(xii) —(C1–4 alkylene)-O-benzoyl,
(xiii) —(C1–4 alkylene)-CONH—(C1–4 alkylene)-NR$^{120}$R$^{130}$, (in which R$^{120}$ and R$^{130}$ have the same meaning as hereinbefore defined),
(xiv) —(C1–4 alkylene)-COO(C1–4 alkylene)—NR$^{120}$R$^{130}$, (in which R$^{120}$ and R$^{130}$ have the same meaning as hereinbefore defined),
(xv) —(C1–4 alkylene)-COO-amidinophenyl,
(xvi) —(C1–4 alkylene)-CONH—(C1–4 alkyl which is substituted by one or two COOR$^{110}$)(in which R$^{110}$ has the same meaning as hereinbefore defined),
(xvii) —C1–4 alkylene)-CONR$^{120}$R$^{130}$, (in which R$^{120}$ and R$^{130}$ have the same meaning as hereinbefore defined), or
(xviii) —(C1–4)alkoxy(C1–4)alkyl;

when A$_0$ is a bond, C1–4 alkylene or vinylene which may be optionally substituted by one or two C1–4 alkyl, and R$^{7c}$ is the formula(ii) as hereinbefore defined, then R$^{50}$, R$^{60}$ and R$^{70}$ do not represent hydrogen), a nontoxic salt thereof or an acid addition salt, or a hydrate thereof.

5. A guanidinophenol derivative represented by the formula (V)

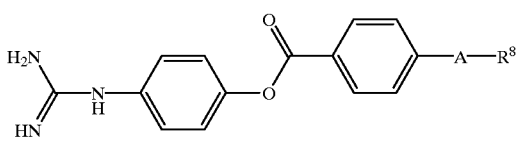
(V)

(wherein A represents a group of the following formula:

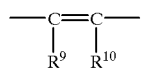

(where R$^9$ and R$^{10}$ each represents independently a hydrogen atom or a C$_{1-4}$ alkyl group), R$^8$ represents a group selected from the following formulae:

i)
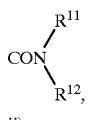

ii)
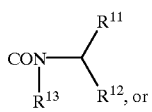

-continued
iii)

(wherein R$^{11}$, R$^{12}$ and R$^{13}$ each represents independently
(1) a hydrogen atom,
(2) a phenyl group,
(3) a C$_{1-4}$ alkyl group substituted by a phenyl group,
(4) a C$_{1-10}$ alkyl group,
(5) a C$_{1-10}$ alkoxyl group,
(6) a C$_{2-10}$ alkenyl group having 1 to 3 double bonds,
(7) a C$_{2-10}$ alkynyl group having 1 to 2 triple bonds,
(8) a group of formula: R$^{15}$—COXR$^{16}$
(where R$^{15}$ represents a single bond or a C$_{1-8}$ alkylene group, X represents an oxygen atom or an NH-group, and R$^{16}$ represents a hydrogen group, a C$_{1-4}$ alkyl group, a phenyl group or a C$_{1-4}$ alkyl group substituted by a phenyl group), or
(9) a C$_{3-7}$ cycloalkyl group;

represents a $_{4-7}$ membered monocyclic heteroring containing 1 to 2 nitrogen atoms,
R$^{14}$ represents a hydrogen, a C4–7 alkyl group substituted by a phenyl group or a group of formula: COOR$^{17}$ (wherein R$^{17}$ represents a hydrogen atom, a C$_{1-4}$ alkyl group or a C$_4$ alkyl group substituted by a phenyl group);
provided that R$^{11}$, R$^{12}$ and R$^{13}$ do not represent simultaneously hydrogen atoms, and when at least one group among R$^{11}$, R$^{12}$ and R$^{13}$ represents a group having a t-butoxycarbonyl group, the other groups do not represent groups having a carboxyl group),
a nontoxic salt thereof or an acid addition salt, or a hydrate thereof.

6. A pharmaceutical comprising, as active ingredient, the compounds represented by the formula (V) according to claim 5, or nontoxic salts, acid addition salts or hydrates thereof.

7. The method according to claim 1, wherein the active ingredient is 6-guanidinohexanoic acid p-ethoxycarbonylphenyl ester, a nontoxic salt thereof or an acid addition salt, or a hydrate thereof.

8. The method according to claim 2, wherein the active ingredient is selected from the group consisting of
p-(p-guanidinobenzoyloxy)phenylacetic acid N,N-dimethyl-carbamoyhnethyl ester,
p-(p-guanidinobenzoyloxy)phenylacetic acid,
p-guanidinobenzoic acid 6-amidinonaphtho-2-yl ester,
and nontoxic salts, acid addition salts or hydrates thereof.

9. The method according to claim 3, wherein the active ingredient is at least one selected from the group consisting of
(1) p-(p-guanidinophenoxycarbonyl)cinnamic acid N-phenyl-N-ethoxycarbonylmethylamide,
(2) p-(p-guanidinophenoxycarbonyl)-α-methylcinnamic acid N-phenyl-N-ethoxycarbonylmethylamide,
(3) p-(p-guanidinophenoxycarbonyl)cinnamic acid N-(2-ethoxycarbonyl)piperidinylamide, (4) p-(p-guanidinophenoxycarbonyl)cinnamic acid N-(3-ethoxycarbonyl)piperidinylamide, (5) p-(p-guanidinophenoxycarbonyl)cinnamic acid N-(4-ethoxycarbonyl)piperidinylamide, (6) p-(p-guanidinophenoxycarbonyl)cinnamic acid N-(2-(S)-ethoxycarbonyl)pyrrolidinylamide, (7) p-(p-guanidinophenoxycarbonyl)cinnamic acid N-(2-(R)-ethoxycarbonyl)pyrrolidinylamide, (8) p-(p-guanidinophenoxycarbonyl)cinnamic acid N-(1-(S)-ethoxycarbonyl-3-ethoxycarbonyl)propylamide, (9) p-(p-guanidinophenoxycarbonyl)-α-methylcinnamic acid N-allyl-N-ethoxycarbonylnethylamide,

(10) p-(p-guanidinophenoxycarbonyl)benzoic acid N-phenyl-N-ethoxycarbonylmethylamide, (11) m-(p-guanidinophenoxycarbonyl)benzenesulfonamide, and nontoxic salts, acid addition salts or hydrates thereof.

10. The method according to claim 4, wherein the active ingredient is at least one selected from the group consisting of (1) p-(p-amidinophenoxycarbonyl)-α-methylcinnamic acid N-allyl-N-ethoxycarbonyhnethylamide, (2) p-(p-amidinophenoxycarbonyl)-α-methylcinnamic acid N-allyl-N-carboxylmethylamide, (3) p-(p-amidinophenoxycarbonyl)-α-methylcinnamic acid N-propargyl-N-ethoxycarbonylmethylamide, (4) p-(p-amidinophenoxycarbonyl)cinnamic acid N-(4-phenylmethyl)piperadinylamide, (5) p-(p-amidinophenoxycarbonyl)phenylpropionic acid N-allyl-N-ethoxycarbonylnethylamide, (6) p-(p-amidinophenoxycarbonyl)-α-methylcinnamic acid N-(1-(S)-ethoxycarbonyl-2-ethoxycarbonylethylthio)ethylamide, (7) p-(p-amidinophenoxycarbonyl)-α-methylcinnamic acid N-ethoxycarbonylmethyl-N-hexylamide, (8) p-(4-amidino-2-methoxycarbonylphenoxycarbonyl)-α-methylcinnamic acid N-allyl-N-ethoxycarbonylmethylamide, (9) p-(p-amidinophenoxycarbonyl)-α-methylcinnamic acid N-(1,1-bis(ethoxycarbonylmethyl)methyl-N-cyclohexylamide,

(10) p-(p-amidinophenoxycarbonyl)a-methylcinnamic acid N-2-ethoxycarbonylethyl-N-3-methoxypropylamide, and nontoxic salts, acid addition salts or hydrates thereof.

11. The compound according to claim 5, which is (1) p-(p-guanidinophenoxycarbonyl)cinnamic acid N-phenyl-N-ethoxycarbonylmethylamide, (2) p-(p-guanidinophenoxycarbonyl)-α-methylcinnamic acid N-phenyl-N-ethoxycarbonylmethylamide, (3) p-(p-guanidinophenoxycarbonyl)cinnamic acid N-(2-ethoxycarbonyl)piperidinylamide, (4) p-(p-guanidinophenoxycarbonyl)cinnamic acid N-(3-ethoxycarbonyl)piperidinylamide, (5) p-(p-guanidinophenoxycarbonyl)cinnamic acid N-(4ethoxycarbonyl)piperidinylamide, (6) p-(p-guanidinophenoxycarbonyl)cinnamic acid N-(2-(S)-ethoxycarbonyl)pyrrolidinylamide, (7) p-(p-guanidinophenoxycarbonyl)cinnamic acid N-(2-(R)-ethoxycarbonyl)pyrrolidinylamide, (8) p-(p-guanidinophenoxycarbonyl)cinnamic acid N-(1-(S)-ethoxycarbonyl-3-ethoxycarbonyl)propylamide, or (9) p-(p-guanidinophenoxycarbonyl)-α-methylcinnamic acid N-allyl-N-ethoxycarbonyhnethylamide.

12. A method for prevention and/or treatment of pulmonary fibrosis, interstitial pneumonitis, cirrhosis, scleroderma, influenza, atherosclerosis, which comprises administering to a patient an effective amount of the guanidinoaliphatic acid derivative represented by the formula (I) according to claim 1, a nontoxic salt thereof or an acid addition salt or a hydrate thereof.

13. A method for prevention and/or treatment of chronic rheumatism, inflammatory intestinal diseases, psoriasis, stomach diseases induced by non-steroidal anti-inflammatory drugs, adult respiratory distress syndrome, myocardial infarction, allergic rhinitis, hemodialysis-inducing neutropenia, late asthma, various inflammatory diseases, allergic diseases, disseminated intravascular coagulation, pancreatitis, severe stages thereof and multiple organ failure which comprises, as an active ingredient, the guanidinophenol derivative represented by the formula (V) according to claim 5, or nontoxic salts, acid addition salts or hydrates thereof.

14. A method for prevention and/or treatment of pulmonary fibrosis, interstitial pneumonitis, cirrhosis, scleroderma, influenza, atherosolerosis, which comprises administering to a patient an effective amount of the guanidinoaliphatic acid derivative represented by the formula (ID) according to claim 2, a nontoxic salt thereof or an acid addition salt or a hydrate thereof.

15. A method for prevention and/or treatment of pulmonary fibrosis, interstitial pneumonitis, cirrhosis, scleroderma, influenza, atherosclerosis, which comprises administering to a patient an effective amount of the guanidinoaliphatic acid derivative represented by the formula (III) according to claim 3, a nontoxic salt thereof or an acid addition salt or a hydrate thereof.

16. A method for prevention and/or treatment of pulmonary fibrosis, interstitial pneumonitis, cirrhosis, scleroderma, influenza, atherosclerosis, which comprises administering to a patient an effective amount of the guanidinoaliphatic acid derivative represented by the formula (IV) according to claim 4, a nontoxic salt thereof or an acid addition salt or a hydrate thereof.

* * * * *